United States Patent [19]

Nagy

[11] 4,095,117

[45] June 13, 1978

[54] CIRCUIT FOR DEFINING THE DYE DILUTION CURVES IN VIVO AND IN VITRO FOR CALCULATING THE CARDIAC BLOOD FLOWRATE VALUE PER MINUTE

[75] Inventor: Ferenc Nagy, Budapest, Hungary

[73] Assignee: Medicor Muvek, Budapest, Hungary

[21] Appl. No.: 701,214

[22] Filed: Jun. 30, 1974

[30] Foreign Application Priority Data

Jun. 30, 1975 Hungary .................... ME 1872

[51] Int. Cl.$^2$ ............................................. G01N 21/28
[52] U.S. Cl. ....................................... 250/564; 356/39
[58] Field of Search ............... 250/564, 565, 214, 573, 250/574; 324/71; 356/39; 128/2 G, 2.05 F

[56] References Cited

U.S. PATENT DOCUMENTS

| 3,715,601 | 2/1973 | Tucker ............................ 356/39 X |
| 3,770,349 | 11/1973 | Legorreta-Sanchez ........... 356/39 X |
| 3,851,156 | 11/1974 | Green ............................. 356/39 X |
| 3,969,024 | 7/1976 | Hashizume et al. ............ 356/39 |
| 3,972,614 | 8/1976 | Johansen et al. .............. 356/39 |

Primary Examiner—David C. Nelms
Assistant Examiner—Vincent Sunderdick

[57] ABSTRACT

The invention concerns a circuit for the determination of the concentration of any component of a liquid containing three different components having different optical properties, for the determination of the concentration sum of all components and of one other component, for the determination of the product and of the quotient which is formed by the third component, and for the calculation of the blood volume per minute of the heart. One or more light sources, a light sensing element, an optical filter and a lens are disposed in the circuit, and also power supply circuits and control circuits. To these are added a signal converting unit or a sensing system operating on three wavelengths other than the isobestic points or on a range containing these points, containing optical measurement channels, and measuring on the transmission or reflection principle.

The signals delivered by the three-channel sensor or by the signal converter, as the case may be, are processed by logarithmatic circuits. The logarithmating circuits are connected to channel amplifiers, and to the latter are connected subtraction circuits and multiplication circuits.

By means of the electronics of suitable construction it is possible to determine in vivo and in vitro both the change with time of the concentration of the dye placed in the blood at any point in the circulatory system, and the volume of the blood.

8 Claims, 31 Drawing Figures

CIRCUIT FOR DEFINING THE DYE DILUTION CURVES IN VIVO AND IN VITRO FOR CALCULATING THE CARDIAC BLOOD FLOWRATE VALUE PER MINUTE

In its broadest aspect, the apparatus according to the invention is suitable for determining the liquid concentration of three components in a liquid containing three components with different optical properties and is suitable for determining the quotient of any two components or the quotient of the sum of two components and of the third component. By means of the apparatus it is also possible to determine the quotient of a product of two components and of the third component. The use of the apparatus is significant in medical laboratories. In first place, it is used for determining the cardiac output and this use will be the subject of the description.

However, the invention relates particularly to a circuit for defining the dye dilution curves in vivo and in vitro for calculating the cardiac output.

With apparatus according to the invention it is possible to measure the change with respect to time of the concentration of the dye introduced at a random place of the circulation - the dye dilution curve - the volume of the blood in the circulation and the oxygen saturation of the blood in vivo (by a photometric transducer applied to the surface of the body) and in vitro by means of a photometric catheter transducer introduced into the circulation or by means of a photometric measurement performed on the blood sample. With these means it is also possible to determine in vivo the pulse curve whose amplitude is independent of the change of oxygen saturation of the blood or it is possible to define in vitro the total content of haemoglobin in the blood per minute.

The quantity of blood pumped through the left ventricle of the heart into the blood circulation is an important characteristic of cardiac performance. This quantity of blood is referred to as "volume per minute". In the course of time, several methods, referred to in their entirety as indication-dilution methods, were developed for determining this quantity of blood. The common feature of these methods is that the dependence on time of the physical characteristics (activity, concentration, temperature) is determined at a selected place of the arterial system by the indicator material (radioactive isotope, dye, cold or warm NaCl solution) which is introduced into the blood, the indicator material being introduced via a vein. The cardiac output can be defined by known methods from the so-called indicator-dilution curve thus obtained.

Because of its advantageous features, the dye dilution system is used in most cases. The apparatus according to the invention comprises a circuit suitable for such a process. Earlier processes and apparatus suffer from several disadvantages. The fundamental causes of these are to be found in the special properties of the object that is to be measured. Blood can be regarded as a liquid containing three components, at least from the point of view of dye dilution examination. These components are: the oxidized haemoglobin ($O_2Hb$), the reduced haemoglobin (red.Hb) and the dye. The first two can assume values which vary physiologically with respect to time, thus making it difficult to determine the concentration-time dependence of the dye. This problem can be explained clearly by reference to FIG. 1 which shows the change with respect to time of the absorption coefficients (in dependence on the wavelength) of the curve expressing $O_2Hb$ (curve 1), the curve expressing red.Hb (curve 2), the curve expressing a blue dye (Evans blue, curve 3) and the curve expressing a green dye (cardio green, curve 4).

The use of the blue dye is restricted because the absorption coefficients of $O_2Hb$ and red.Hb differ widely at the wavelength of their maximum absorption. The accuracy of determining the time dependence of the dye concentration is therefore greatly influenced by the change of oxygen saturation which occurs in the course of measurement. The dye dilution curve thus obtained is therefore used only for qualitative measurements and not for calculating the cardiac output. The difference between the absorption coefficients of $O_2Hb$ and red.Hb at their maximum absorption wavelength of green dyes is not very great, in other words in an ideal case the measurement of the discrete wavelength (805 nm) at the isosbestic point is zero. However, the bandwidth of the measuring channel in such apparatus can in practice be reduced at most down to 10-15 nm. The interference effect of oxygen saturation must therefore be taken into account. This interference effect can be reduced by appropriate selection of the quantity of injected dye of a specific value. A dye of this kind is therefore used for the dilution curve to calculate the cardiac output. In view of the fact that the injected quantity of dye is limited by methodic and physiological factors, it follows that the accuracy achieved in such a case is also only limited. A further disadvantage of apparatus known hitherto is due to the fact that the end concentration of the dye in the blood sample must be determined before and after the measurement in the case of in vivo measurements. (This value is designated by $C_{3V}$ in the dye dilution curve). The examination thus becomes complex, the error sources increase (two samples must be taken and the samples must be prepared and measured) and a second apparatus should therefore be used.

A further disadvantage of the apparatus known hitherto is that in the case of in vivo measurements the measuring accuracy is impaired, more particularly any further mechanized processing of the dye dilution curve, namely due to the pulse curve which is superimposed on the useful indication. Solutions which are acceptable to a greater or lesser degree and promise a reliable result are adopted to avoid this defect and lead to success only if different conditions are given. However, this interference effect in every case gives rise to a problem.

By means of the apparatus according to the invention it is possible to determine the dye dilution curve and the correct value of the end concentration to calculate the cardiac output, apart from permitting the use of any desired dye; changes of oxygen saturation or of the pulse curve which take place in the course of in vivo and in vitro measurements can be eliminated so that the measurement is not subject to any interference.

With the apparatus it is also possible to determine, in the case of in vivo measurements, the pulse curve whose amplitude is independent of a change of oxygen saturation and, on the basis of a knowledge of the total haemoglobin content of the patient's blood, it is possible to determine the blood volume in the circulation and in the case of in vitro measurements it is possible to determine the oxygen saturation of the blood, the total haemoglobin content and the volume of the blood in the circulation. The apparatus according to the invention is also suitable for observing elimination through the liver in vivo of the dye introduced into the blood circulation, that is to say for investigating so-called liver functions.

To convert the signals the apparatus according to the invention contains three light sources which operate simultaneously on a wavelength which deviates from the isosbestic point or points or include the said point or points. The apparatus also contains a light sensing element a sensor or sensor transducer unit incorporating an optical filter and lens, adapted to measure on the transmission principle or reflection measuring principle and having an optical measuring channel. It also contains circuits for feeding and controlling the said unit. Advantageously, the signals are converted by circuits which co-operate with the same light-sensitive element in time multiplex operation, contain one or more solid-state light sources, an optical filter and a lens, as well as control and power circuits and are adapted for storing and filtering the sampled signal, the said circuits incorporating sensor or signal transducer units. The electrical signals which are supplied through the three-channel sensors or through the signal transducer are processed by circuits with logarithmic functions. The outputs of these circuits are connected to channel amplifiers for adjusting the characteristic features which are identical for optical reasons. The logarithmic effect can be achieved by providing a light sensor comprising one or more photovoltaic cells which are advantageously terminated by a working resistor which is larger by 50 kohms. A voltage which is proportional with a good approximation to the logarithm of the intensity of the light that strikes the photovoltaic cells will in this case appear at the terminals of the said light sensing element.

The general circuit arrangement comprises the subtracting circuits that follow the channel amplifiers, the subtracting circuits and those containing the scale, scale adjusting circuits and multiplying circuits or an electrical network comprising a combination of the above and on whose outputs appear the electrical signals which are proportional to the concentration values or to the sums thereof. The individual circuits are constructed as follows in accordance with their function:

As already mentioned, the apparatus comprises one or more light sources, light sensing elements, optical filters and lenses as well as three sensor elements or signal transducing units adapted to measure by the transmission or reflection principle and containing optical measuring channels and adapted to operate in the wavelength range which deviates from the isosbestic points or includes them, as well as logarithmic function generators L1, L2, L3 connected thereto and channel amplifiers which are connected to the latter circuits. Of the said channel amplifiers, the output of the first channel amplifier A1 is directly connected to one input of a first subtracting circuit H1, the output of the second channel amplifier A2 is directly connected to one input of a second subtracting circuit H2, and the output of the third channel amplifier A3 is directly connected to one input of a third subtracting circuit H3. The output of the first channel amplifier A1 is connected through a branch and via a multiplier circuit M1 to the other one input of the third subtracting circuit H3, the output of the second channel amplifier A2 is connected through a second multiplier circuit M2 to the other input of the first subtracting circuit H1, the output of the third channel amplifier A3 is connected through a further multiplier circuit M3 to the other input of the second subtracting circuit H2. Of the subtracting circuits H1, H2, H3 which are directly connected to the channel amplifiers A1, A2 and A3, the output of the first subtracting circuit H1 is directly connected to one input of a fourth subtracting circuit H4, the output of the second subtracting circuit H2 is directly connected to one input of a first subtracting and scale adjusting circuit U1, the output of the third subtracting circuit H3 is directly connected to one input of the second subtracting and scale adjusting circuit U2. The output of the first subtracting circuit H1 is connected through a fourth multiplying circuit M4 to the other input of the second subtracting and scale adjusting circuit U2, the output of the third subtracting circuit H3 is connected to the other input of the fourth subtracting circuit H4 through a fifth multiplier circuit M5. The output of the fourth subtracting circuit H4 is connected on the one hand directly to the input of a scale setting circuit G1 and on the other hand, through a sixth multiplier circuit M6, to the other input of the first subtracting and scale setting circuit U1. The output of the scale setting circuit G1 is connected to one input of a summing network $\Sigma$ and to the display unit DP. The output of the first subtracting and scale setting circuit U1 is connected to a first input of a quotient-forming and multiplying circuit MD and to the display unit DP, the output of the second subtracting and scale setting circuit U2 being connected on the one hand to the second input of the summing network $\Sigma$ and on the other hand to the display unit DP and to a first input of the circuit D which forms the quotient. The output of the summing network $\Sigma$ is connected on the one hand to the quotient-forming and multiplying circuit and on the other hand to the second input of the quotient-forming circuit D and to the display unit DP. An adjustable potentiometer P4 for precision control is connected to the third input of the quotient-forming and multiplying circuit MD. The output of the quotient-forming and multiplying circuit MD is connected to the display unit DP and to the third input of the quotient-forming circuit D. A second adjustable potentiometer P5 for precision control is connected to the fourth input of the quotient-forming circuit D, the three remaining outputs of the quotient-forming circuit being connected to the display unit DP (see FIG. 3).

The apparatus according to the invention can also be constructed so that the output of the first channel amplifier A1 is directly connected to a subtracting circuit H5 which is first in series, the output of the second channel amplifier A2 is directly connected to a first input of a second subtracting circuit H6, and the output of the third channel amplifier A3 is directly connected to one input of a third subtracting circuit H7. The output of the first channel amplifier A1 is connected via a multiplying circuit M7 to the second input of the second subtracting circuit H6, the output of the second channel amplifier A2 is connected through a first multiplier circuit M8 to the other input of the third subtracting circuit H7 and through a second multiplying circuit M9 to the second input of the subtracting circuit H5 which is the first in series. The output of the subtracting circuit H5, which is the first in series, is directly connected to a first input of a fourth subtracting circuit H8, the output of the second subtracting circuit H6 is directly connected to a first input of a subtracting and scale setting circuit U3, and the output of the third subtracting circuit H7 is directly connected to a first input of the second subtracting and scale setting circuit U4, the output of the first subtracting circuit H5 being connected through a multiplier circuit M10 to the second input of the second subtracting and scale setting circuit U4, the output of the third subtracting circuit H7 being connected through a further multiplying circuit M11 to the second input of a further subtracting circuit H8 which is the fourth in series. The output of the fourth subtracting circuit H8 is directly connected on the one hand to the input of a scale setting circuit G2 and on the other hand, through a further multiplying circuit M12, to the other input of the first subtracting and scale setting circuit U3 which is the first in series. The output of the scale setting circuit G2 is connected to the display unit DP and to one input of a summing network Σ. The output of the first subtracting and scale setting circuit U3 is connected to the display unit DP and to one input of a quotient-forming and multiplying circuit MD. The output of the second subtracting and scale setting circuit U4 is connected to the second input of the above-mentioned quotient-forming and multiplying circuit MD and is also connected to the second input of the summing network Σ as well as to the display unit DP but the output of the summing network Σ is connected on the one hand to the display unit DP and on the other hand to the third input of the quotient-forming and multiplying circuit MD (which contains a total of six inputs). Adjustable precision potentiometers P4, P5, P6 are connected to the fourth, fifth and sixth inputs of the quotient-forming and multiplying circuit MD, the outputs thereof being connected to the display unit. The multiplying circuit performs a multiplication the factors of which are formed by the electrical signals which reach the input of the said circuit and by the linear combination of the absorption coefficients of the component that is to be measured and by a constant number. In the case of multiplication with a number which is smaller than unity, the said multiplying circuit is embodied as a potentiometer and/or a voltage divider comprising fixed resistors. It can also be constructed as an emitter follower or an amplifier stage comprising a potentiometer and/or fixed resistors and being connected downstream of the voltage divider; if multiplication is performed with a number which is greater than unity the said module is constructed as an amplifier stage. The subtracting circuit performs the subtraction of two electric signals which are supplied to its input. The circuit is embodied as a subtracting operational amplifier or a summing operational amplifier. The subtracting and scale setting circuit performs the subtraction of one electric signal from the other, both of which are applied to the inputs of the said circuit. The circuit can be constructed as a subtracting operational amplifier or as a summing operational amplifier. The subtracting and scale setting circuit subtracts one electric signal from the other supplied to its inputs. The correct scale of an electric signal which is proportional to the given concentration is set up by appropriate selection of the amplification factor. This embodiment of the said module corresponds to the subtracting circuit.

The scale of the electric signal which is proportional to the given concentration is set up by appropriate selection of the amplification factor of this circuit. This circuit is embodied as an operational amplifier.

The summing network adds the electric signals applied to its inputs. This circuit is embodied as a adding operational amplifier or a subtracting operational amplifier.

Further processing of the electric signals which are proportional to the individual concentrations or sums of the said concentrations is performed in the quotient-forming circuit which divides two electric signals that are variable with respect to time or is performed in the quotient-forming and multiplying circuit which divides two signals which vary with respect to time or by multiplication of the result thereof with an electric signal which is variable with respect to time or not variable with respect to time (having unity value).

Depending on the particular embodiment, the apparatus comprises setting potentiometers which provide signals or apply precision control for the amount of injected dye, for the total haemoglobin content of the patient or the final concentration of the dye. Indicating instruments to indicate the measured values are also provided.

The invention will now be explained hereinbelow by reference to diagrams or drawings which illustrate the individual embodiments and in which.

All the drawings show the circuits in diagrammatic form.

The features of the apparatus will be related to the case of the most frequently employed cardio green dye and to the transducer which is placed upon the surface of the body for measuring in vivo and adapted to operate by the transmission principle. Measurement performed by the transmission principle can be mathematically exact, measurement performed by the reflection principle on the other hand is subject to several limitations and can merely be regarded as an approximate method.

In describing the relationship a simplification is introduced which does not however influence the nature of the invention but according to which the individual concentration values as well as the dependence on time of the measured thickness of the sample as well as measurement itself is performed at a discrete wavelength.

The wavelengths of the individual measuring channels (see FIG. 1) are given in the following sequence:

$\lambda_1 = 650$ nm
$\lambda_2 = 820$ nm
$\lambda_3 = 900$ nm.

The following terms will be used:
$C_1$ $O_2Hb$ concentration
$C_2$ red.Hb concentration
$C = C_1 + C_2$ Total haemoglobin content concentration
$C_3$ Dye concentration
$\Sigma_1, \Sigma_2, \Sigma_3$ absorption coefficients of $O_2Hb$, of red.Hb and the dye at wavelength $\lambda_1$.

$\alpha_1, \alpha_2, \alpha_3$ O$_2$Hb, red.Hb and dye absorption coefficients at wavelength $\lambda_2$.

Figure 1:
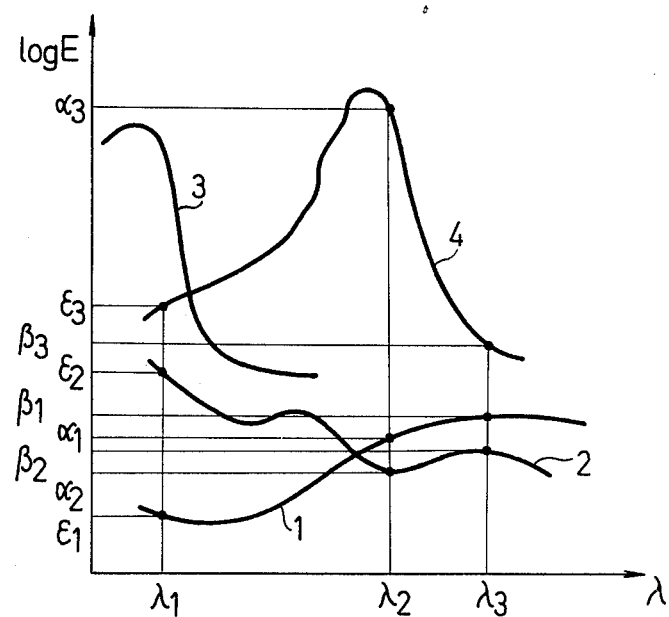
FIG. 1 is a graph showing the change with respect to time of the extinction factors of $O_2Hb$ and red.Hb and the dyes of Evans blue and cardio green, plotted against the wavelength $\lambda$.

$\beta_1, \beta_2, \beta_3$ O$_2$Hb, red.Hb and dye absorption coefficients at wavelength $\lambda_3$ (see FIG. 1).

$\phi_{o1}, \phi_{o2}, \phi_{o3}$ Intensity of the light incident in the sample under measurement on wavelengths $\lambda_1, \lambda_2$ and $\lambda_3$.

$\phi_1, \phi_2, \phi_3$ Intensity of the light transmitted through the sample at wavelengths $\lambda_1, \lambda_2$ and $\lambda_3$.

$d$ Thickness of the measured sample.

The relationships are described by reference to FIG. 3. The electrical signals supplied by the transducer T are connected to the input of the logarithmic function generators L1, L2 and L3. (The transducer T contains one or more light sources, fed by the feed circuit TM, an optical filter, a light sensing element and three optical measuring channels for retaining and filtering the obtained signal in the event of operation based on the time-multiplex principle).

The signals which are connected to the inputs of the logarithmic function generators are characterized on the basis of the Lambert-Beer law as follows:

$$-\epsilon_1 C_1 d - \epsilon_2 C_2 d - \epsilon_3 C_3 d \ \phi = \phi_{o1}^{10} \quad \quad 1.$$

$$-\alpha_1 C_1 d - \alpha_2 C_2 d - \alpha_3 C_3 d \ \phi = \phi_{o2}^{10} \quad \quad 2.$$

$$-\beta_1 C_1 d - \beta_2 C_2 d - \beta_3 C_3 d \ \phi = \phi_{o3}^{10} \quad \quad 3.$$

After the logarithmic operation performed in the logarithmic function generators the above expressions assume the following form:

$$\log \phi_1 = \log \phi_{o1} - \epsilon_1 C_1 d - \epsilon_2 C_2 d - \epsilon_3 C_3 d \quad \quad 4.$$

$$\log \phi_2 = \log \phi_{o2} - \alpha_1 C_1 d - \alpha_2 C_2 d - \alpha_3 C_3 d \quad \quad 5.$$

$$\log \phi_3 = \log \phi_{13} - \beta_1 C_1 d - \beta_2 C_2 d - \beta_3 C_3 d \quad \quad 6.$$

The electrical signals corresponding to the equation are supplied to the inputs of the channel amplifiers A1, A2, A3 which are adjusted for identical optical characteristics. Electrical signals of identical magnitude appear at the outputs of the channel amplifiers A1, A2 and A3 if the measured sample has identical optical properties in the three wavelength ranges. The outputs of the channel amplifiers A1, A2, A3 are set to zero when the sample to be compensated by the potentiometers P1, P2 and P3 is placed in the sensor. After performing the function, the following relationships are obtained:

$$\log \frac{\phi_1}{\phi_{o1}} = -\epsilon_1 C_1 d - \epsilon_2 C_2 d - \epsilon_3 C_3 d \quad \quad 7.$$

$$\log \frac{\phi_2}{\phi_{o2}} = -\alpha_1 C_1 d - \alpha_2 C_2 d - \alpha_3 C_3 d \quad \quad 8.$$

$$\log \frac{\phi_3}{\phi_{o3}} = -\beta_1 C_1 d - \beta_2 C_2 d - \beta_3 C_3 d \quad \quad 9.$$

The equations 7, 8 and 9 are multiplied by the multiplier circuits M1, M2 and M3 with the constants $\beta_3/\epsilon_3$, $\epsilon_3/\alpha_3$ and $\alpha_1/\beta_1$:

$$\frac{\beta_3}{\epsilon_3} \log \frac{\phi_1}{\phi_{o1}} = -\epsilon_1 \frac{\beta_3}{\epsilon_3} C_1 d - \epsilon_2 \frac{\beta_3}{\epsilon_3} C_2 d - \beta_3 C_3 d \quad \quad 10.$$

$$\frac{\epsilon_3}{\alpha_3} \log \frac{\phi_2}{\phi_{o2}} = -\alpha_1 \frac{\epsilon_3}{\alpha_3} C_1 d - \alpha_2 \frac{\epsilon_3}{\alpha_3} C_2 d - \epsilon_3 C_3 d \quad \quad 11.$$

-continued $$\frac{\alpha_1}{\beta_1} \log \frac{\phi_3}{\phi_{o3}} = -\alpha_1 C_1 d - \beta_2 \frac{\alpha_1}{\beta_1} C_2 d - \beta_3 \frac{\alpha_1}{\beta_1} C_2 d \quad \quad 12.$$

Equation 7 is subtracted from the equation by means of the subtracting circuit H1;

$$\frac{\epsilon_3}{\alpha_3} \log \frac{\phi_2}{\phi_{o2}} - \log \frac{\phi_1}{\phi_{o1}} = \quad \quad 13.$$

$$(\epsilon_1 - \alpha_1 \frac{\epsilon_3}{\alpha_3}) C_1 d + (\epsilon_2 - \alpha_2 \frac{\epsilon_3}{\alpha_3}) C_2 d$$

The following terms can be introduced:

$$Z_1 = \frac{\epsilon_3}{\alpha_3} \log \frac{\phi_2}{\phi_{o2}} - \log \frac{\phi_1}{\phi_{o1}} \quad \quad 14.$$

$$K_1 = \epsilon_1 - \alpha_1 \frac{\epsilon_3}{\alpha_3} \quad \quad 15.$$

$$K_2 = \epsilon_2 - \alpha_2 \frac{\epsilon_3}{\alpha_3} \quad \quad 16.$$

After introducing these terms, equation 13 can be written as follows:

$$Z_1 = K_1 C_1 d + K_2 C_2 d \quad \quad 17.$$

Only two unknown concentration values will be found on the right hand side of the equation, i.e. in the output signal of the subtracting circuit H$_1$.

Equation 8 is subtracted from equation 12 by means of the subtracting circuit H2 as follows:

$$\frac{\alpha_1}{\beta_1} \log \frac{\phi_3}{\phi_{o3}} - \log \frac{\phi_2}{\phi_{o2}} = \quad \quad 18.$$

$$(\alpha_2 - \beta_2 \frac{\alpha_1}{\beta_1}) C_2 d + (\alpha_3 - \beta_3 \frac{\alpha_1}{\beta_1}) C_3 d$$

The following terms can then be introduced:

$$Z_2 = \frac{\alpha_1}{\beta_1} \log \frac{\phi_3}{\phi_{o3}} - \log \frac{\phi_2}{\phi_{o2}} \quad \quad 19.$$

$$K_3 = \alpha_2 - \beta_2 \frac{\alpha_1}{\beta_1} \quad \quad 20.$$

$$K_4 = \alpha_3 - \beta_3 \frac{\alpha_1}{\beta_1} \quad \quad 21.$$

Equation 18 therefore assumes the following form:

$$Z_2 = K_3 C_2 d + K_4 C_3 d \quad \quad 22.$$

Only two unknown concentration values will be found on the right-hand side of the equation, i.e. in the output signal of the subtraction circuit H2.

Equation 9 is subtracted from Equation 10 by means of the subtracting circuit H3 as follows:

$$\frac{\beta_3}{\epsilon_3} \log \frac{\phi_1}{\phi_{o1}} - \log \frac{\phi_3}{\phi_{o3}} = (\beta_1 - \epsilon_1 \frac{\beta_3}{3}) C_1 d + (\beta_2 - \epsilon_2 \frac{\beta_3}{3}) C_2 d \quad \quad 23.$$

The following terms can then be introduced:

$$Z_3 = \frac{\beta_3}{3} \log \frac{\phi_1}{\phi_{o1}} - \log \frac{\phi_3}{\phi_{o3}} \qquad 24.$$

$$K_5 = \beta_1 - \epsilon_1 \frac{\beta_3}{3} \qquad 25.$$

$$K_6 = \beta_2 - \epsilon_2 \frac{\beta_3}{3} \qquad 26.$$

After introducing the above-mentioned terms, Equation 23 assumes the following form:

$$Z_3 = K_5 C_1 d + K_6 C_2 d \qquad 27.$$

Only two unknown concentration values will be found on the right-hand side of the equation or in the output signal of the subtraction circuit H3.

Equation 27 which expresses the output signal of the subtraction circuit H3 must be multiplied with a constant $K_1/K_5$ by means of the multiplier circuit M5, and Equation 17, which merely expresses the output signal of the subtraction circuit H1, must be subtracted by means of the subtraction circuit H4. The output signal of the subtraction circuit can then be expressed as follows:

$$(K_1/K_5) Z_3 - Z_1) = (K_1/K_5) K_6 - K_2) C_2 d \qquad 28.$$

It is a condition for correct operation that the gain of the subtraction circuits H1, H2, H3 and H4 shall be equal (this has not been indicated in the written equations). The scale of the selected signal is set up by the scale setting circuit G1 which is connected to the output of the subtraction circuit H4. Due to the presence of a factor $\sigma_2$ the output signal of the scale setting circuit G1 can be expressed by the following equation:

$$\sigma_2 (K_1/K_5) Z_3 - Z_1) = \sigma_2 (K_1/K_5) K_6 - K_2) C_2 d \qquad 29.$$

If the left-hand side of the equation is replaced by Y and the constant factor of the $C_2$ is replaced by the constant K, the equation will take the following form:

$$Y = K C_2 d \qquad 30.$$

Equation 17, which merely expresses the output signal of the subtraction circuit H1, must be multiplied with a constant value of $K_6/K_2$ by means of the multiplier circuit M4 and the Equation 27, which merely expresses the output signal of the subtracting circuit H3, must be subtracted by means of the subtracting and scale setting circuit U2. The equation can then be written as follows with respect to the factor $\sigma_1$ which sets the scale:

$$_1(Z_1 \frac{K_6}{K_2} - Z_3) = {}_1(K_1 \frac{K_6}{K_2} - K_5) C_1 d \qquad 31.$$

If the left-hand side of the equation is substituted by X and the constant factor of $C_1$ is replaced by a constant K, the equation can then be written as:

$$X = K C_1 d \qquad 32.$$

Equation 28, which expresses the output signal of the subtraction circuit H4, is thus multiplied by means of the multiplier circuit M6 with a constant $K_3/(K_6 (K_1/K_5) - K_2)$ and is subtracted from Equation 22 (which represents the output signal of the subtracting circuit H2) by means of the subtraction and scale setting circuit U1. In view of the scale setting factor $\sigma_3$, the equation then takes the following form:

$$_3 [\frac{K_3}{K_6 \frac{K_1}{K_5} - K_2} (\frac{K_1}{K_5} Z_3 - Z_1) - Z_2] = {}_3 K_4 C_3 d \qquad 33.$$

If the left-hand side of the equation is replaced by W and the constant factor of $C_3$ is replaced by K, the equation will take the following form:

$$W = K C_3 d \qquad 34.$$

To summarize, it may be noted that an electrical signal of the same scale and proportional to $C_2$ appears on the output of the scale setting circuit G1, a like signal proportional to $C_1$ appears at the output of the subtracting and scale setting circuit U2 and a like signal proportional to $C_3$ appears at the output of the subtracting and scale setting circuit U1. The output signals of the scale setting circuit G1 and of the subtracting and scale setting circuit U2 are summated by the summing network $\Sigma$ as follows:

$$X + Y = K (C_1 + C_2) d = K C d \qquad 35.$$

Due to the dependence of the value d on time, in the case of in vivo measurements, a pulse curve whose amplitude is independent on the change of oxygen saturation will appear at the output of the summing network $\Sigma$. The output signal of the summing network $\Sigma$ as well as the signal of the subtracting and scale setting circuit U2 are transferred to the quotient-forming circuit D which forms a signal proportional to the oxygen saturation S by forming the quotient from both signals:

$$S = (X/X + Y) = (K C_1 d/K(C_1 + C_2) d) = (C_1/C) \qquad 36.$$

This expression no longer includes d, the value of S is therefore no longer changed by any alteration with respect to time of the thickness in the measured sample.

The signal which is proportional to the concentration $C_3$ and is independent on the thickness d of the sample is determined by the quotient-forming and multiplier circuit MD from the output signal of the summing network $\Sigma$ as well as from the output signal of the subtracting and scale setting circuit U1 and from an electrical signal K'C which is proportional to the total haemoglobin content of the patient's blood and is set by the potentiometer P4 which provides for precision regulation:

$$(K C_3 d/K C d) K'C = K'C_3 \qquad 37.$$

Figure 2:
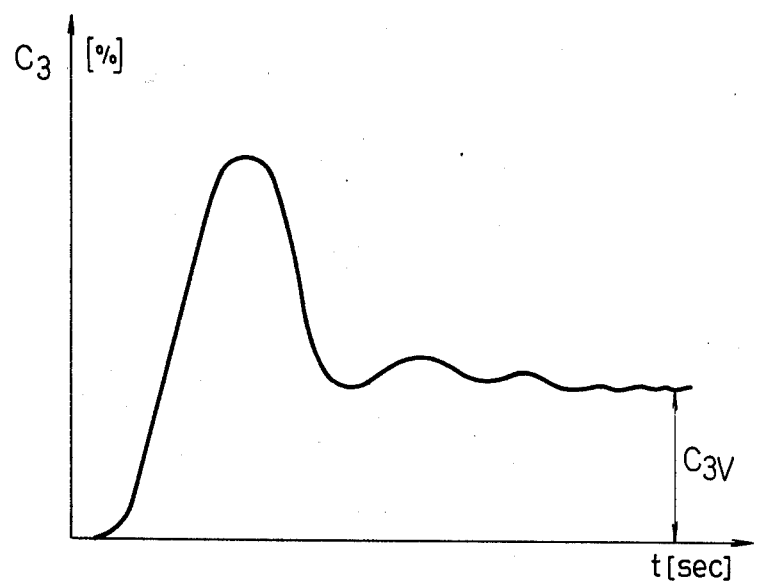
FIG. 2 is a characteristic dye dilution curve (the concentration values are plotted on the ordinate and the time is plotted on the abscissa).

Equation 37 therefore provides an expression for the change with respect to time of the dilution curve that characterizes the dye concentration and is unaffected by the change of oxygen saturation and by any disturbance of the pulse curve. After a specific period of time following the dye injection, the dye distributes in the blood and the final concentration value is formed, see also FIG. 2 - $C_{3r}$. In view of this, Equation 37 takes the following form:

$$(K\ C_{3\nu}d/K\ C\ d)\ K'C' = K'\ C_{3\nu} \qquad 38.$$

A signal proportional to the amount of blood in the blood circulation is determined by the quotient-forming circuit D (see FIG. 3) from the output signal $K'C_{3\nu}$ of the quotient-forming and multiplier circuit MD and from the signal $K''Qb$ which is set by the precision potentiometer P5 and is proportional to the amount of dye injected into the blood of the patient:

$$(K''Qb/K'C_{3\nu}) = K_o(Qb/C_{3\nu}) = K_oV \qquad 39.$$

The signals which are proportional to the concentration values $C_1$, $C_2$, $C_3$ of the concentration sum $C_1 + C_2 = C$ and are proportional to the oxygen saturation and the blood volume in the circulation can be successively displayed or recorded on the display unit DP or can be so displayed and recorded in parallel if several display units are used.

Figure 4:
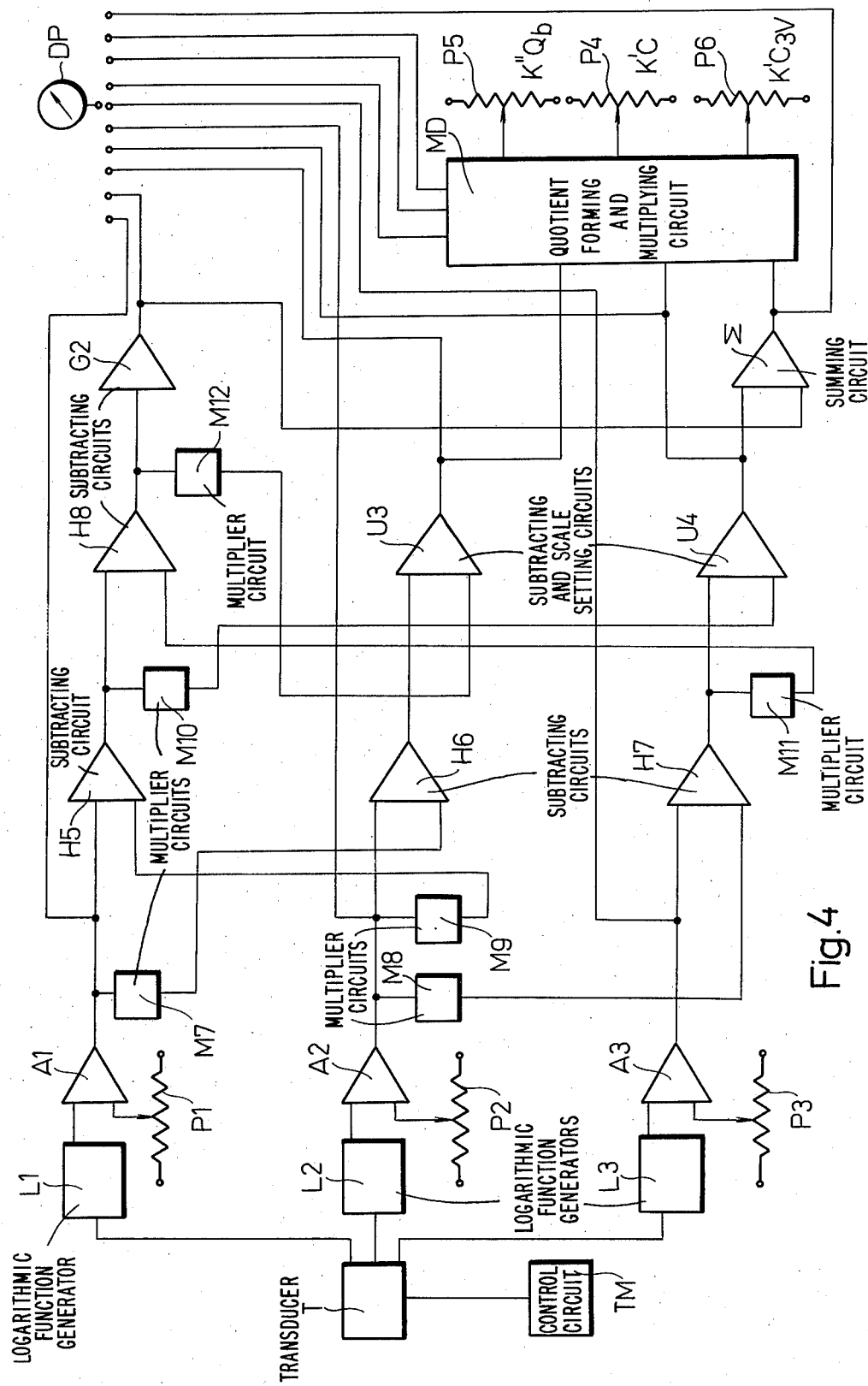
FIG. 4 shows the circuit of another embodiment of the invention.

Another embodiment of the invention is illustrated in FIG. 4. The operation thereof is described by reference to Equations 7, 8 and 9.

If Equation 7 is multiplied with the multiplier circuit M7 by the constant value $\alpha_1/\epsilon_1$ and if the Equation 8 is subtracted therefrom by means of the subtraction circuit H6, the result will be:

$$\frac{\alpha_1}{\epsilon_1}\log\frac{\phi_1}{\phi_{o1}} - \log\frac{\phi_2}{\phi_{o2}} = (\alpha_2 - \epsilon_2\frac{\alpha_1}{1})\ C_2d + (\alpha_3 - \epsilon_3\frac{\alpha_1}{\epsilon_1})\ C_3d \qquad 40.$$

Only two unknown concentration values appear on the left-hand side of the equation or in the output signal of the subtraction circuit H6.

Equation 8 must be multiplied with the multiplier circuit M9 by the constant value $\epsilon_3/\alpha_3$ and Equation 7 must be subtracted therefrom by means of the subtraction circuit H5 to yield:

$$\frac{\epsilon_3}{\alpha_3}\log\frac{\phi_2}{\phi_{o2}} - \log\frac{\phi_1}{\phi_{o2}} = (\epsilon_1 - \alpha_1\frac{\epsilon_3}{\alpha_3})\ C_1d + (\epsilon_2 - \alpha_2\frac{\epsilon_3}{\alpha_3})\ C_2d \qquad 41.$$

Only two unknown concentration values occur on the right-hand side of the equation or in the output signal of the subtraction circuit H5. Equation 8 must be multiplied with the multiplier circuit M8 by a constant value of $\beta_3/\alpha_3$ and Equation 9 subtracted therefrom by means of the subtraction circuit H7 to yield:

$$\frac{\beta_3}{\alpha_2}\log\frac{\phi_2}{\phi_{o2}} - \log\frac{\phi_3}{\phi_{o3}} = (\beta_1 - \alpha_1\frac{\beta_3}{\alpha_3})\ C_1d + \qquad 42.$$
$$(\beta_2 - \alpha_2\frac{\beta_3}{\alpha_3})\ C_2d$$

Only two unknown concentration values are found on the right-hand side of the equation or in the output signal of the subtraction circuit H7.

Figure 3:
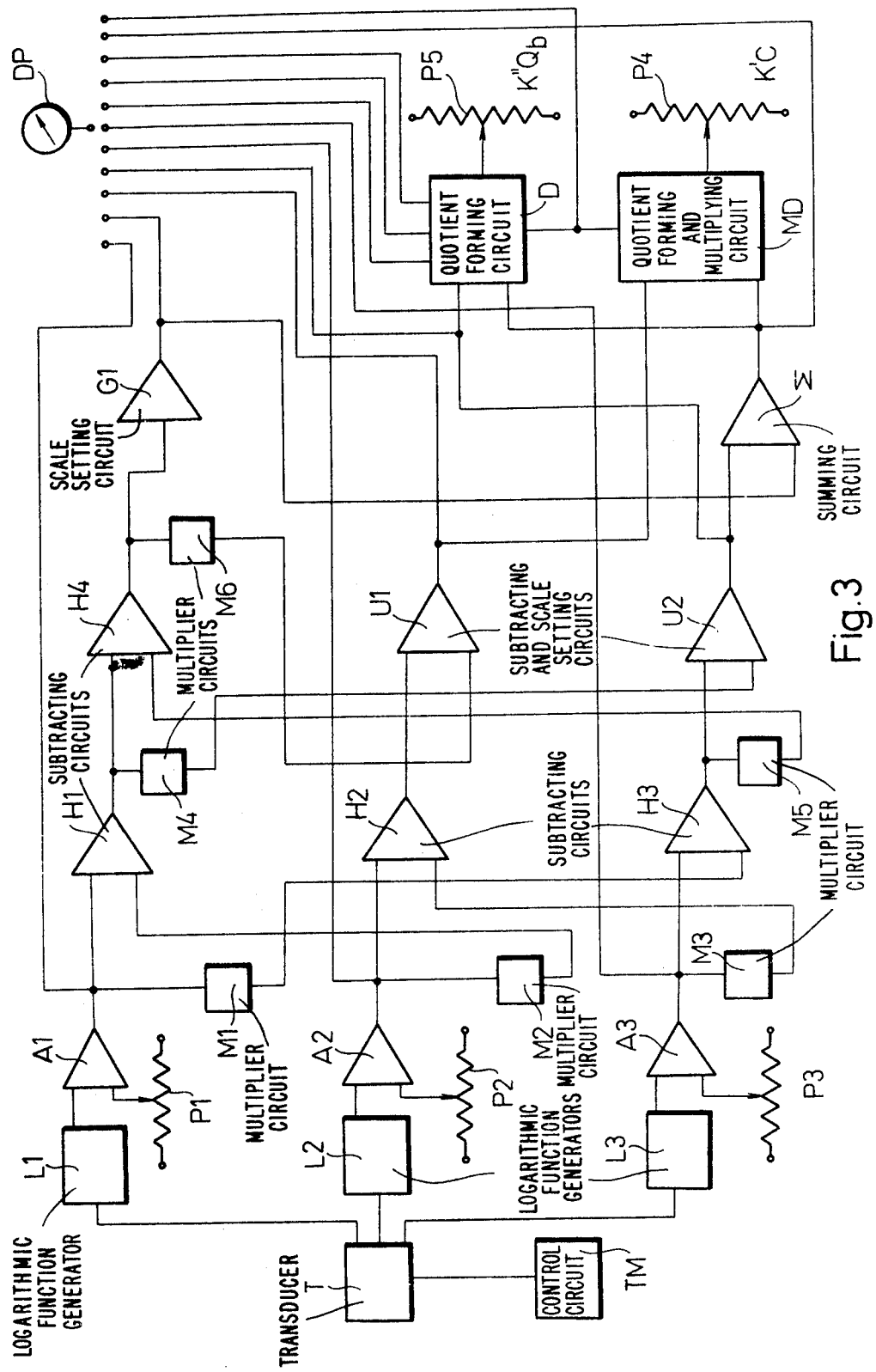
FIG. 3 shows a circuit of one embodiment of the invention.

By analogy to FIG. 3, the remaining operations are performed by means of the multiplier circuits M10, M11 and M12, the subtracting circuits H5, H6, H7 and H8, the subtracting and scale setting circuits U3 and U4, the scale setting circuit G2 and the summing network Σ.

The signal which is proportional to $C_2$ is produced at the output of the scale setting circuit G2:

$$Y = K\ C_2d \qquad 30.$$

A signal which is proportional to $C_3$ is produced at the output of the subtraction and scale setting circuit U3:

$$W = K\ C_3d \qquad 34.$$

A signal which is proportional to $C_1$ appears at the output of the subtraction and scale setting circuit U4:

$$X = K\ C_1d \qquad 32.$$

A signal which is proportional to the sum $C_1 + C_2$ appears at the output of the summing network Σ:

$$X + Y = K\ C\ d \qquad 35.$$

An electrical signal which is independent of the thickness $d$ of the measured sample and is proportional only to the concentration $C_3$ is obtained from the output signals of the quotient-forming and multiplying circuit MD, the subtracting and scale setting circuit U3 and the summing network Σ and from the output signal $K'C$ which is set by means of the potentiometer P4 and is proportional to the known haemoglobin content of the patient.

$$(K\ C_3\ d/K\ C\ d)\ K'C = K'C_3 \qquad 37.$$

$$(K\ C_{3\nu}d/K\ C\ d)\ K'C = K'C_{3\nu} \qquad 38.$$

The value of $K'C_{3\nu}$ can be displayed or the value $K'C_{3\nu}$ set by the precision potentiometer P6 together with the value $K''Q_b$, set by the precision potentiometer P5, can be connected to the quotient-forming and multiplier circuit MD. The blood volume in the circulation is thus determined by forming the quotient from the two signals.

$$\frac{K''Q_b}{K'C_{3\nu}} = K_o\frac{Q_b}{C_{3\nu}} = K_oV \qquad 39.$$

The oxygen saturation of the blood is determined in like manner in the quotient-forming and multiplier circuit MD, namely from the output signal of the subtracting and scale setting circuit U4 from the output signal of the summing network Σ:

$$S = \frac{X}{X+Y} = \frac{K\ C_1d}{K\ C\ d} = \frac{C_1}{C} \qquad 36.$$

The concentration values C1, C2, C3 and C as well as the values of S and V can be displayed and recorded successively on the same display unit or parallel to each other if several display units are provided.

Different embodiments of the invention will be explained by reference to FIGS. 5, 6, 7, 8, 9, 10, 11, 12, 13 and 14. The computing operations explained by reference to FIGS. 3 and 4 can be applied correspondingly to these embodiments.

Figure 5:
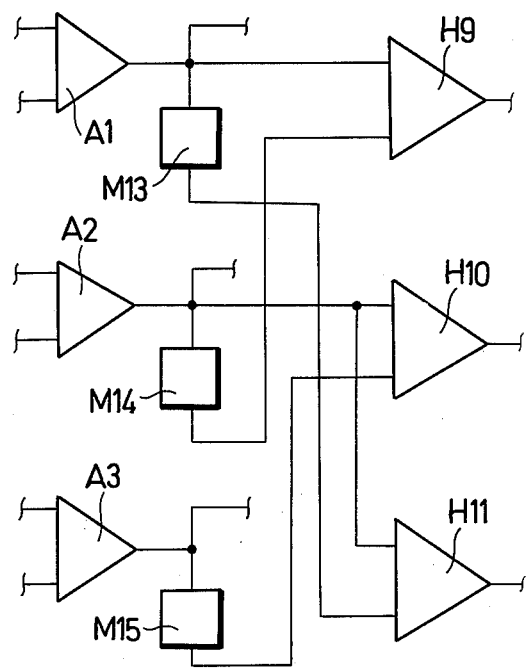
FIGS. 5–10 show further embodiments.

In the embodiment according to FIG. 5, the output of the channel amplifier A1 is connected directly to one input of a subtracting circuit H9, the output of the channel amplifier A2 being directly connected to the input of the subtracting circuit H10 and H11. In like manner, the channel amplifier A1 is connected through the multiplier circuit M13, the channel amplifier A2 is connected through the multiplier circuit M14 and the channel amplifier A3 is connected through the multiplier circuit M15 to the other input of the subtraction circuits H11, H9 and H10 respectively. The output signal of the subtraction circuits H9, H10 and H11 can be expressed through functions $f(C_2,C_3)$, $f(C_1,C_2)$ which contain two unknown concentration values and can also be expressed by the function $f(C_1,C_2)$.

Figure 6:
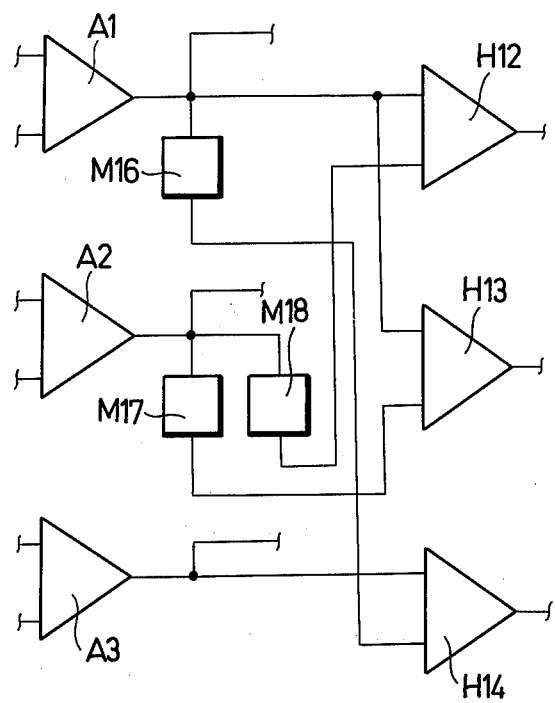

According to FIG. 6 the output of the channel amplifier A1 is directly connected to one output of each of the subtraction circuits H12 and H13, but the channel amplifier A3 is directly connected to one input of the subtraction circuit H14. The channel amplifier A1 is also connected through the multiplier circuit M16 and the channel amplifier A2 is connected through the multiplier circuit M17 and M18 to the other input of the subtraction circuits H14, H13 and H12. The output signals of the subtraction circuits H12, H13 and H14 are expressed in sequence by the functions f($C_1$, $C_3$), f($C_1$, $C_2$) and f($C_1$, $C_2$).

Figure 7:
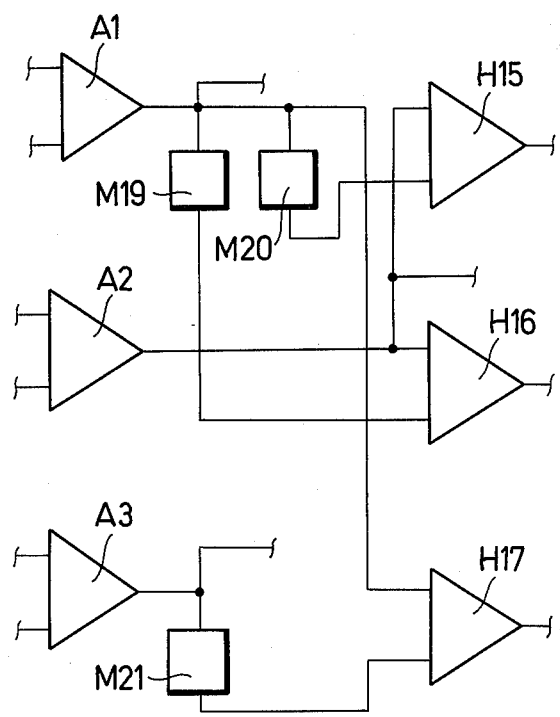

According to FIG. 7, the output of the channel amplifier A1 is directly connected to one input of the subtraction circuit H17 and the output of the channel amplifier A2 is directly connected to one input of the subtraction circuit H15 and H16.

Furthermore, the channel amplifiers A1 and A3 are connected via the multiplyier circuits M19 and M20 and the channel amplifier A3 is connected through the multiplier circuit M21 to the other inputs of the subtraction circuits H15, H16 and H17. The output signals of the subtraction circuits H15, H16 and H17 can be expressed in sequence by the functions $f(C_2, C_3)$, $f(C_1, C_2)$ and by $f(C_1, C_2)$.

Figure 8:
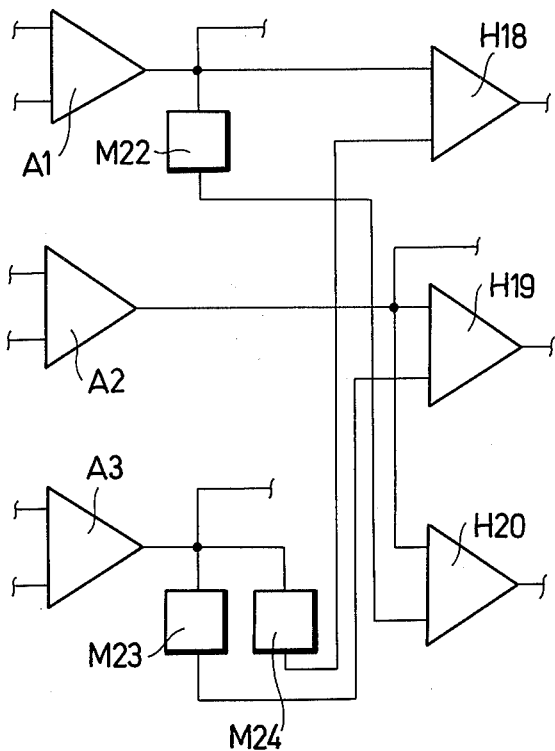

According to FIG. 8, the output of the channel amplifier A1 is connected to one input of the subtraction circuit H18 and the output of the channel amplifier A2 is directly connected to one input of the subtraction circuit H19 and H20. The channel amplifier A1 is connected on the one hand through the multiplier circuit M22 and the channel amplifier A3 through the multiplier circuits M23 and M24 to to the other input of the subtracting circuits H20, H19 and H18. The output signals of the subtracting circuits can be expressed in sequence by the functions $f(C_1, C_2)$ and $f(C_1, C_2)$ or $f(C_2, C_3)$.

Figure 9:
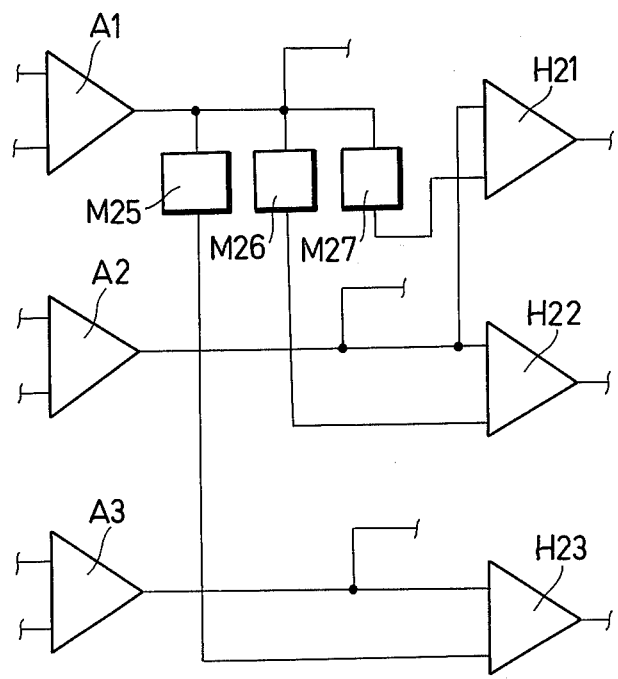

According to FIG. 9, the output of the channel amplifier A2 is directly connected to one input of the subtracting circuit H21 and H22, the output of the channel amplifier A3 is directly connected to one input of the subtracting circuit H23 but the output of the channel amplifier A1 is connected through the multiplier circuits M25, M26 and M27 to the other inputs of the subtracting circuits H23, H22 or H21.

The output signals of the subtracting circuits can be expressed in sequence by the functions $f(C_1, C_3)$, $f(C_1, C_2)$ or $f(C_1, C_2)$.

Figure 10:
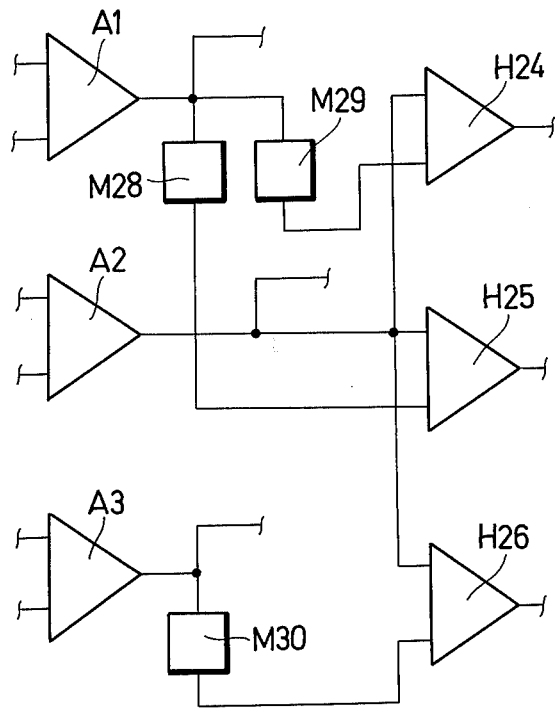
Figure 11:
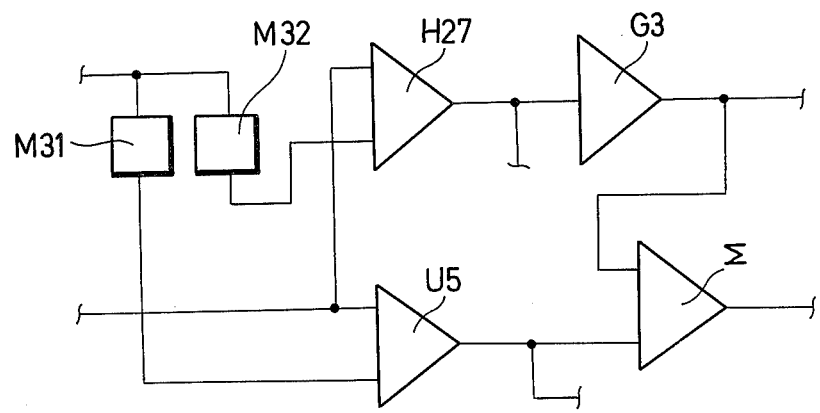
FIGs. 11–14 show circuits of the embodiments illustrated in FIGS. 3–10.

According to FIG. 10, the output of the channel amplifier A2 is directly connected on the one hand to one input of each of the subtracting circuits H24, H25 and H26 and is connected on the other hand through the multiplier circuits M28 or M29 and the output of the channel amplifier A3 is connected through the multiplier circuit M30 to the other input of the subtracting circuit H26. the output signals of the subtracting circuits H24, H25 and H26 can each be expressed in sequence by the functions $f(C_2, C_3)$, $f(C_1, C_2)$ or $f(C_1, C_2)$.

The signals which correspond to the individual concentration values can be produced in accordance with the embodiments illustrated in FIGS. 11, 12, 13 and 14 from the output signals of the subtracting circuits which follow the channel amplifiers, said subtracting circuits representing a linear equation with two unknowns.

One input of subtracting circuit H27 and of the scale setting circuit and subtracting circuit U5 is directly connected to the output of the subtracting circuit H3 according to FIG. 3. The output of the subtracting circuit H1 is connected through the multiplying circuits M31 and M32 to the input of the subtracting and scale setting circuit U2 and to the subtracting circuit H27. A signal proportional to $C_1$ appears at the output of the subtracting and scale setting circuit U5 and a signal proportional to $C_2$ appears at the output of the subtracting circuit H27. The scale setting circuit G3 is provided for setting up the correct scale of the signal produced at the output of the subtracting circuit H27 and the summing network $\Sigma$ (see FIGS. 3 and 11) is provided to form the signal which is proportional to C. If an input of the subtracting circuit H27 and of the subtracting and scale setting circuit U5 is directly connected to the output of the subtracting circuit H7 (FIG. 4) and if the output of the subtracting circuit H5 is connected through the multiplying circuits M31 and M32 to the other input of the subtracting and scale setting circuit U5 and to the subtracting circuit H27, a signal which is proportional to $C_1$ will be obtained from the output of the subtracting and scale setting circuit U5, but a signal which is proportional to $C_2$ will be obtained from the output of the subtracting circuit H27. A scale setting circuit G3 is provided for correct adjustment of the output signal from the subtracting circuit H27 and the summing network $\Sigma$ (see FIGS. 4 and 11) one input of which is connected to the output of the subtracting and scale setting circuit U5, is provided to form the signal which is proportional to C. The output of the scale setting circuit G3 is connected to the other input of the summing network $\Sigma$ (see FIGS. 4 and 11).

One input of the subtracting circuit H27 and of the subtracting and scale setting circuit U5 is connected directly to the output of the subtracting circuit H10 (FIG. 5). On the other hand, the output of the subtracting circuit H11 is connected through the multiplier circuits M31 and M32 to the other input of the subtracting circuits H27 and subtracting and scale setting circuit U5. A signal which is proportional to $C_1$ is produced at the output of the subtracting and scale setting circuit U5 and a signal which is proportional to $C_2$ is produced at the output of the subtracting circuit H27, that means of the scale setting circuit G3 (see FIGS. 5 and 11).

One input of the subtracting circuit H27 and of the subtracting and scale setting circuit U5 can be connected directly to the output of the subtracting circuit H13, the output of the subtracting circuit H14 being connected through the multiplying circuits M31 and M32 to the other input of the subtracting and scale setting circuit U5 and of the subtracting circuit H27. A signal which is proportional to $C_2$ is produced at the output of the subtracting and scale setting circuit U5 and a signal which is proportional to $C_1$ is produced at the output of the scale setting circuit G3 that means of the subtracting circuit H27 (see FIGS. 6 and 11).

The output of the subtracting circuit H19 (according to FIG. 8) is connected directly to one input of the subtracting circuit H27 or of the subtracting and scale setting circuit U5 and the output of the subtracting circuit H20 is connected through the multiplier circuits M31 and M32 to the other input of the subtracting and scale setting circuit U5 and that of the subtracting circuit H27. A signal which is proportional to $C_1$ is thus produced at the output of the subtracting and scale setting circuit U5 and a signal which is proportional to $C_2$ is produced at the output of the subtracting circuit H27 and of the scale setting circuit G3 (see FIGS. 8 and 11).

The output of the subtracting circuit H22 (FIG. 9) can be connected directly to one input of the subtracting circuit H27 and to the subtracting and scale setting circuit U5 while the output of the subtracting circuit H23 can be connected via the multiplying circuits M31 and M32 to the other input of the subtracting and scale setting circuit U5 and of the subtracting circuit H27. In this case, a signal which is proportional to $C_1$ is produced at the output of the subtracting and scale setting circuit U5 and a signal which is proportional to $C_2$ is produced at the output of the subtracting circuit H27 and of the scale setting circuit G3 (see FIGS. 9 and 11).

The output of the subtracting circuit H25 (according to FIG. 10) is connected directly to one input of the subtracting circuit H27 and of the subtracting and scale setting circuit U5 and the output of the subtracting circuit H26 is connected via the multiplying circuits M32 and M31 to the other input of the subtracting circuit H27 or of the subtracting and scale setting circuit U5. In this case, a signal which is proportional to $C_1$ is produced at the output of the subtracting and scale setting circuit U5 and a signal which is proportional to $C_2$ is produced at the output of the subtracting circuit H27 and of the scale setting circuit G3 (see FIGS. 10 and 11).

The output of the subtracting circuit H10 (see FIG. 5) is connected directly on the one hand to one input of the subtracting and scale setting circuit U6 and on the other hand is connected through the multiplier circuit 33 to one input of the subtracting circuit H28. The other input of the subtracting circuit H28 and of the subtracting and scale setting circuit U6 can be connected to the output of the subtracting circuit H11. In this case, a signal which is proportional to $C_1$ will be produced at the output of the subtracting and scale setting circuit U6 and a signal which is proportional to $C_2$ will be produced at the output of the subtracting circuit H28 and of the scale setting circuit G4. A summing network $\Sigma$ (see FIGS. 5 and 12) one input of which is connected to the output of the subtracting and scale setting circuit U6 while the other input is connected to the output of the scale setting circuit G3 is provided to form a signal which is proportional to C.

The output of the subtracting circuit H13 according to FIG. 6 is directly connected on the one hand to one input of the subtracting and scale setting circuit U6 and on the other hand via the multiplier circuit M33 to the subtracting circuit H28, while the input thereof of can be connected to the output of the subtracting circuit H14 and on the other hand the input of the subtracting and scale setting circuit U6 can be connected via the multiplier circuit M34. In this case, a signal which is proportional to $C_2$ will be produced at the output of the subtracting and scale setting circuit U6 and a signal which is proportional to $C_1$ will be produced at the output of the subtracting circuit H28 and of the scale setting circuit G4 (see FIGS. 6 and 12).

The output of the subtracting circuit H16 (according to FIG. 7) can be directly connected on the one hand to one input of the subtracting and scale setting circuit U6 and on the other hand one input of the subtracting circuit H28 can be connected through the multiplier circuit M33 to the output of the subtracting circuit H17, but the other input of the subtracting circuit H28 can be connected on the other hand through a multiplier circuit M34 to the input of the subtracting and scale setting circuit U6. In this case, a signal proportional to $C_1$ is produced at the output of the subtracting and scale setting circuit U6 and a signal proportional to $C_2$ is produced at the output of the subtracting circuit H28 and of the scale setting circuit G4 (see FIGS. 7 and 12).

The output of the subtracting circuit H18 (FIG. 8) is connected directly to one input of the subtracting circuit H28, on the one hand through the subtracting and scale setting circuit U6, and on the other hand through the multiplier circuit M23, but is connected to the other input of the subtracting and scale setting circuit U6 partially through the multiplier circuit M34 and partially through the subtracting circuit H28. In this case, a signal proportional to $C_1$ is produced at the output of the subtracting and scale setting circuit U6 and a signal which is proportional to $C_2$ is produced at the output of the subtracting circuit H28 and of the scale setting circuit G4 (see FIGS. 8 and 12).

The output of the subtracting circuit H22 according to FIG. 9 can be connected directly to one input of the subtracting circuit H28, on the one hand through the subtracting and scale setting circuit U6 and on the other hand through the multiplier circuit M23, while the other input of the subtracting and scale setting circuit is connected to the output of the subtracting circuit H23, namely through the multiplier circuit M34 and through the subtracting circuit H28. In this case, a signal which is proportional to $C_1$ will be produced at the output of the subtracting and scale setting circuit U6 and a signal which is proportional to $C_2$ will be produced at the output of the subtracting circuit H28 and of the scale setting circuit G4 (see FIGS. 9 and 12).

The output of the subtracting circuit H25 according to FIG. 10 can be connected directly to one input on the other hand of the subtracting and scale setting circuit U6 and on the other hand, through the multiplier circuit M33, to the subtracting circuit H28. The other input of the subtracting circuit H28 on the one hand is connected to the output of the subtracting circuit H26 and on the other hand the other input of the subtracting and scale setting circuit U6 is connected thereto through the multiplier circuit M34. In this case, a signal which is proportional to $C_1$ is produced at the output of the subtracting and scale setting circuit U6 and a signal which is proportional to $C_2$ is produced at the output of the subtracting circuit H28 and of the scale setting circuit G4 (see FIGS. 10 and 12).

Figure 12:
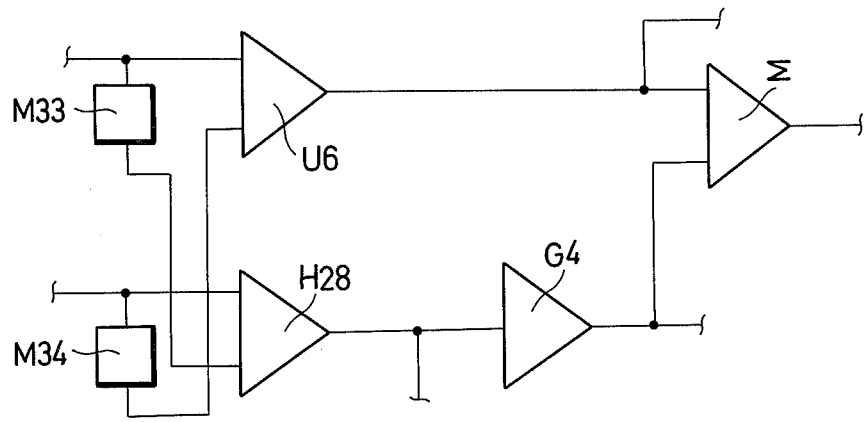
Figure 13:
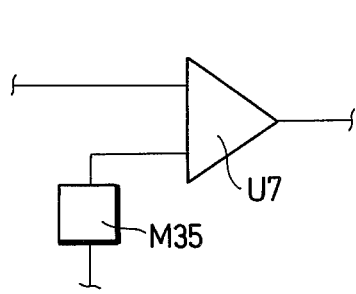
Figure 14:
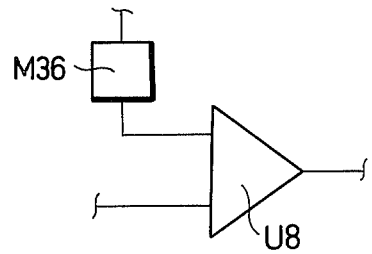

The value of the remaining concentration is determined by the circuits in accordance with FIGS. 13 and 14. The output of the subtracting circuit H9 (FIG. 5) or H12 (FIG. 6) or H15 (FIG. 7) or H20 (FIG. 8) or H21 (FIG. 9) or H24 (FIG. 10) is connected directly to one input of the subtracting and scale setting circuit U7. These subtracting circuits are also directly connected to the channel amplifier. The output of the subtracting circuit H27 (FIG. 11) or H28 (FIG. 12) is connected to the other input of the subtracting and scale setting circuit U7, the last-mentioned output being connected through the multiplier circuit M35. In this case, a signal which is proportional to the concentration $C_3$ will appear at the output of the subtracting and scale setting circuit U7.

The output of the subtracting circuits H9 (FIG. 5) or H12 (FIG. 6) or H15 (FIG. 7) or H20 (FIG. 8) or H21

(FIG. 9) or H24 (FIG. 10) which follows the channel amplifiers is connected through the multiplier circuit M35 to one input of the subtracting and scale setting circuit U8 while the other input thereof is directly connected to the output of the subtracting circuit H27 (FIG. 11) or H28 (FIG. 12). In this case, a signal which is proportional to the concentration $C_3$ is produced at the output of the subtracting and scale setting circuit U8.

Other embodiments of the invention are illustrated in FIGS. 15 to 31. The operation of these embodiments is explained by reference to the circuit according to FIG. 15 and based on Equations 7, 8 and 9.

If Equation 7 is multiplied with the multiplier circuit M37 by the constant value $\alpha_1/\epsilon_1$ and if the Equation 8 is subtracted therefrom by means of the subtracting circuit H30, the result will be:

$$\frac{\alpha_1}{\epsilon_1} \log \frac{\phi_1}{\phi_{01}} - \log \frac{\phi_2}{\phi_{02}} = \qquad 43.$$
$$(\alpha_2 - \epsilon_2 \frac{\alpha_1}{1})C_2 d + (\alpha_3 - \epsilon_3 \frac{\alpha_1}{1})C_3 d$$

By using the designations introduced earlier the following relationship is obtained:

$$Z_4 = K_7 C_3 d + K_8 C_3 d \qquad 44.$$

By multiplying Equation 8 with a multiplier circuit M39 by a constant a value $\epsilon_3/\alpha_3$ and by subtracting therefrom the Equation 7 by means of the subtracting circuit H29, the following expression will be obtained:

$$\frac{\epsilon_3}{\alpha_3} \log \frac{\phi_2}{\phi_{02}} - \log \frac{\phi_1}{\phi_{01}} = \qquad 45.$$
$$(\epsilon_1 - \alpha_1 \frac{\epsilon_3}{\alpha_3})C_1 d + (\epsilon_2 - \alpha_2 \frac{\epsilon_3}{\alpha_3})C_2 d$$

The following relationship is obtained by using the terms which were introduced earlier:

$$Z_5 = K_9 C_1 d + K_{10} C_2 d \qquad 46.$$

If Equation 8 is multiplied with the multiplying circuit M38 by a constant value $\beta_3/\alpha_3$ and if Equation 9 is subtracted therefrom by means of the subtracting circuit H32, the following relationship will be obtained:

$$\frac{\beta_3}{\alpha_3} \log \frac{\phi_2}{\phi_{o2}} - \log \frac{\phi_3}{\phi_{o3}} = \qquad 47.$$
$$(\beta_1 - \alpha_1 \frac{\beta_3}{\alpha_3}) C_1 d + (\beta_2 - \alpha_2 \frac{\beta_3}{\alpha_3}) C_2 d$$

The following relationship will be obtained by using the terms which were introduced earlier:

$$Z_6 = K_{11}C_1 d + K_{12}C_2 d \qquad 48.$$

If Equation 9 is multiplied with the multiplying circuit M40 by a constant value $\alpha_1/\beta_1$ and if Equation 8 is subtracted therefrom by means of the subtracting circuit M31, the following relationship will be obtained:

$$\frac{\alpha_1}{\beta_1} \log \frac{\phi_3}{\phi_{o3}} - \log \frac{\phi_2}{\phi_{o2}} = \qquad 49.$$
$$(\alpha_2 - \beta_2 \frac{\alpha_1}{\beta_1}) C_2 d + (\alpha_3 - \beta_3 \frac{\alpha_1}{\beta_1}) C_3 d$$

By introducing the simplifying term, the following relationship is obtained:

$$Z_7 = K_{13}C_2 d + K_{14}C_3 d \qquad 50.$$

Equations 44, 46, 48 or 50 which express the output signals of the subtracting circuits H30, H29, H32 and H31 contain only two unknown concentration values.

If Equation 44 is multiplied with the multiplying circuit M42 by a constant value $K_{13}/K_7$ and if Equation 50 is subtracted therefrom by means of the subtracting and scale setting circuit U10, the following relationship will be obtained:

$$\sigma'_3 (Z_4 \frac{K_{13}}{K_7} - Z_7) = \sigma'_3 (K_8 \frac{K_{13}}{K_7} - K_{14}) C_3 d \qquad 51.$$

The term $\sigma_3'$ is a factor for setting the scale. By using the terms introduced earlier, the equation takes the following form:

$$W = K C_3 d \qquad 52.$$

A signal which is and proportional to the concentration $C_3$ will therefore be produced at the output of the subtracting and scale setting circuit U10.

If Equation 48 is multiplied with the multiplying circuit M43 by a constant value $K_9/K_{11}$ and if Equation 46 is subtracted therefrom with the subtracting and scale setting circuit U11, the following relationship will be obtained:

$$\sigma'_3 (Z_6 \frac{K_9}{K_{11}} - Z_5) = \sigma'_2 (K_{12} \frac{K_9}{K_{11}} - K_{10}) C_2 d \qquad 53.$$

By using the terms introduced earlier, the equation will take the following form:

$$Y = K C_3 d \qquad 54.$$

A signal which is proportional to the concentration $C_2$ is produced at the output of the subtracting and scale setting circuit. If Equation 46 is multiplied with the multiplying circuit M41 by a constant value $K_{12}/K_{10}$ and if Equation 48 is subtracted therefrom by means of the subtracting and scale setting circuit U9, the following relationship will be obtained:

$$\sigma'_1 (Z_5 \frac{K_{12}}{K_{10}} - Z_6) = \sigma'_1 (K_9 \frac{K_{12}}{K_{10}} - K_{11}) C_1 d \qquad 55.$$

The term $\sigma_1'$ is a factor which refers to the scale setting. By using the terms introduced earlier, the following relationship will be obtained:

$$X = K C_1 d \qquad 56.$$

A signal which is proportional to the concentration $C_1$ is produced at the output of the subtracting and scale setting circuit U9.

Equation 52, 54 and 55 are processed as already explained in accordance with FIGS. 3 and 4. These operations also apply accordingly to the embodiments according to FIGS. 16–31.

Figure 16:
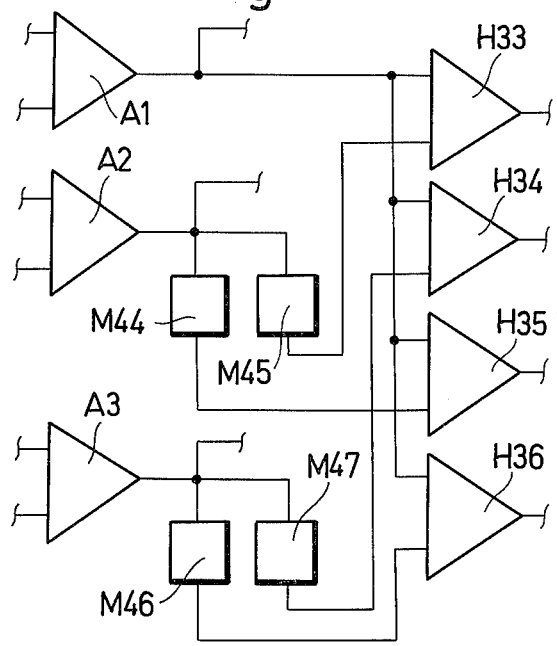

According to FIG. 16, the output of the channel amplifier A1 is directly connected to one input of each of the subtracting circuits H33, H34, H35 and H36, while the other input of the subtracting circuits H33 and H35 is connected to the channel amplifier A2 via the multiplier circuits M45 and M44 and the channel amplifier A3 is connected to the other input of the subtracting circuits H34 and H36 through the multiplier circuits M47 and M46. The output signals of the subtracting circuits H33, H34, H35 and H36 can be expressed in sequence by the functions $f(C_1, C_3)$, $f(C_1, C_2)$, $f(C_2, C_3)$ and $f(C_1, C_2)$.

Figure 17:
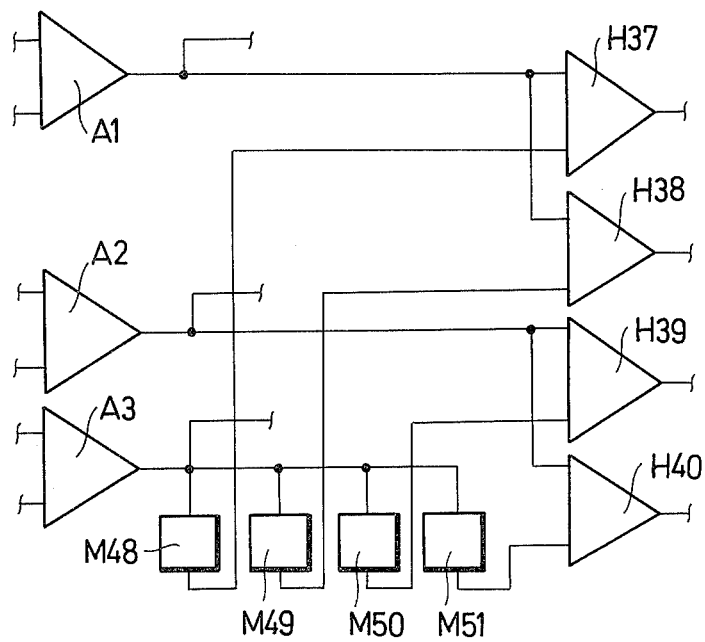

The output of the channel amplifier A1 according to FIG. 17 is connected directly to one input of the subtracting circuits H37 and H38 and the output of the channel amplifier A2 is directly connected to one input of the subtracting circuits H39 and H40. The output of the channel amplifier A3 is directly connected through the multiplier circuits M48, M49, M50 and M51 to the other input of the subtracting circuits H37, H38, H39 and H40. The output signals of the subtracting circuits H37, H38, H39 and H40 can be expressed by the corresponding functions $f(C_1, C_2)$, $f(C_1, C_2)$, $f(C_2, C_3)$ and $f(C_2, C_3)$.

Figure 18:
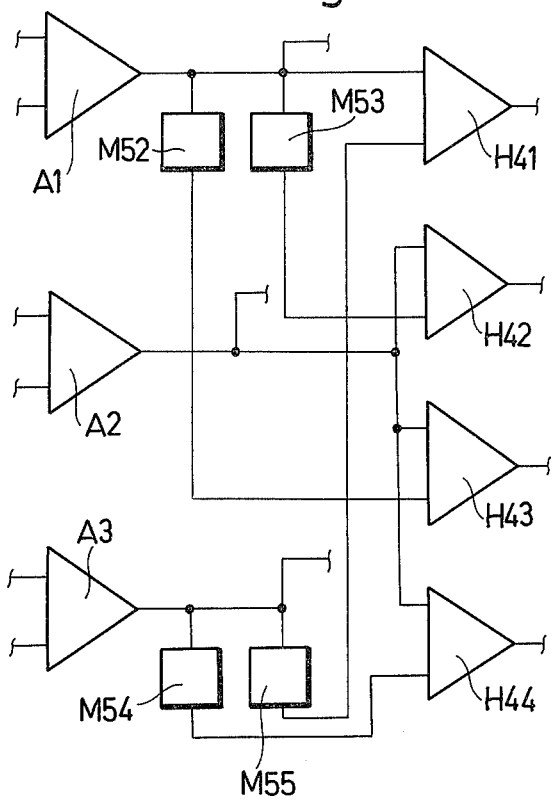

According to FIG. 18, the amplifier output of the channel amplifier A1 is connected directly to one input of the subtracting circuit H41 and the amplifier output of the channel amplifier A2 is directly connected to one output of each of the subtracting circuits H42, H43 and H44, while the output of the channel amplifier A1 is connected through the multiplier circuits M52 and M53 to the other input of the subtracting circuits H43 and H42 and the output of the channel amplifier A3 is connected through the multiplier circuits M54 and M55 to the other input of the subtracting circuits H44 and H41. The output signals of the subtracting circuits H41, H42, H43 and H44 can be expressed accordingly by the functions $f(C_1, C_2)$, $f(C_1, C_2)$, $f(C_2, C_3)$ and $f(C_2, C_3)$.

Figure 19:
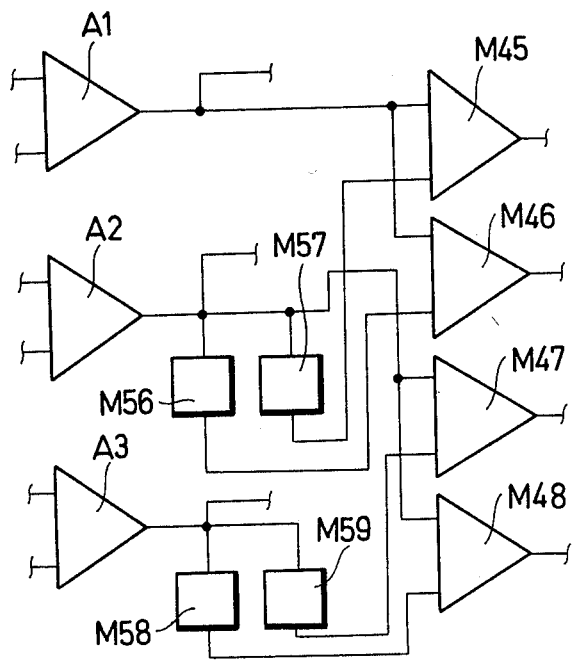

The amplifier output of the channel amplifier A1 according to FIG. 19 is directly connected to one input of the subtracting circuits H45 and H46 and the amplifier output of the channel amplifier A2 is directly connected to one input of the subtracting circuits H47 and H48.

The output of the channel amplifier A2 is also connected through the multiplier circuits M56 and M57 to the other input of the subtracting circuit H46 and H45 and the output of the channel amplifier A3 is connected through the multiplier circuits M58 and M59 to the other input of the subtracting circuits H48 and H47. Depending on the sequence, the output signals of the subtracting circuits H45, H46, H47 and H48 can be expressed by the functions $f(C_1, C_2)$, $f(C_2, C_3)$, $f(C_1, C_2)$ and $f(C_2, C_3)$.

Figure 20:
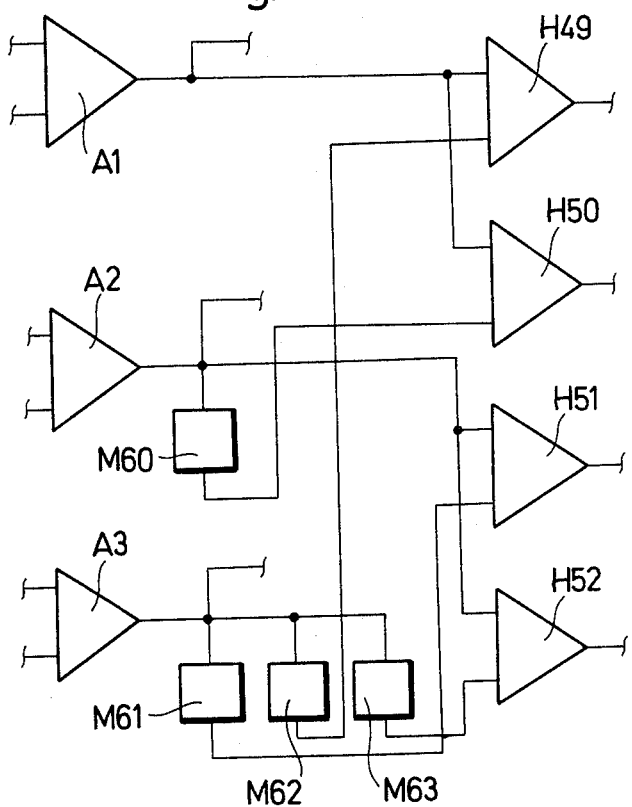

The output of the channel amplifier A1 according to FIG. 20 is directly connected to one input of each of the subtracting circuits H49 and H50 and the output of the channel amplifier A2 is directly connected to one output of each of the subtracting circuits H51 and H52. The output of the channel amplifier A2 is connected through the multiplier circuit M60 to the other input of the subtracting circuit H50 and the output of the channel amplifier A3 is connected through the multiplier circuits M61, M62 and M63 to the other input of the subtracting circuits H51, H49 and H52.

Depending on the sequence, the output signals of the subtracting circuits H49, H50, H51, H52 can be expressed by the functions $f(C_1, C_2)$, $f(C_2, C_3)$, $f(C_1, C_2)$ and $f(C_2, C_3)$.

Figure 21:
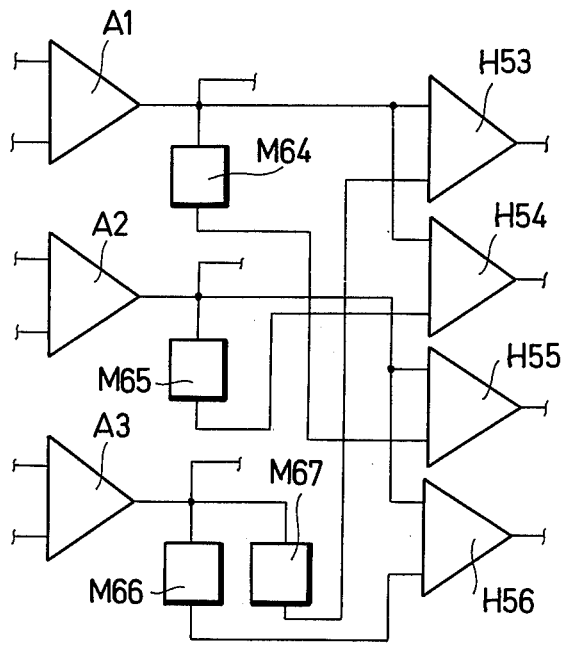

In another embodiment according to FIG. 21, the output of the channel amplifier A1 is directly connected to one input of each of the subtracting circuits H53 and H54 and the output of the channel amplifier A2 is directly connected to the one input of the subtracting circuits H55 and H56. At the same time, the output of the channel amplifier A1 is connected through the multiplier circuit M64 to the other input of the subtracting circuit H55, the output of the channel amplifier A2 is connected through the multiplier circuit M65 to the other input of the subtracting circuits H54 while the output of the channel amplifier A# is connected through the multiplier circuits M66 and M67 to the other input of the subtracting circuits H56 and H53. Depending on the sequence, the output signals of the subtracting circuits H53, H54, H55, H56 can be expressed by the functions $f(C_1, C_2)$, $f(C_1, C_2)$, $f(C_2, C_3)$ and $f(C_2, C_3)$.

Figure 22:
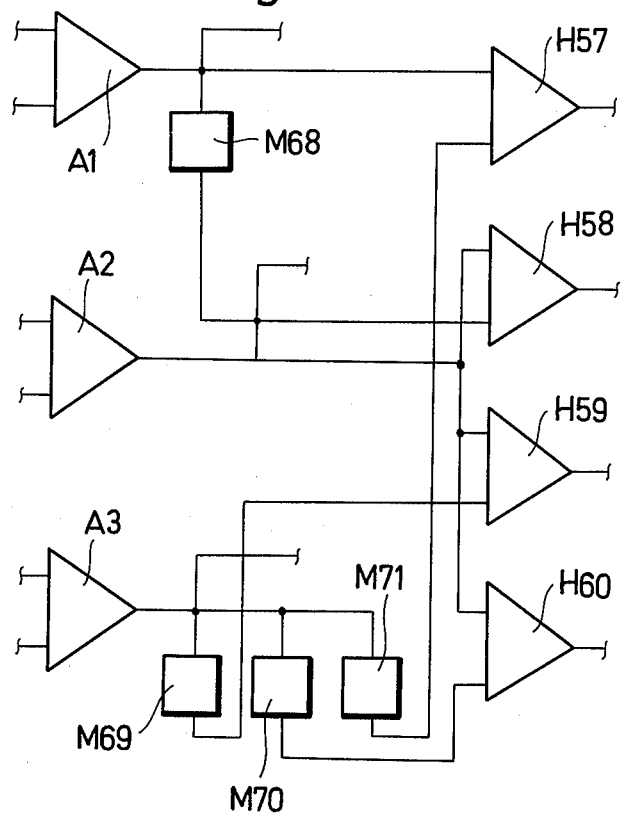

In considering another embodiment according to FIG. 22 it will be seen that the output of the channel amplifier A1 is connected directly to one input of the subtracting circuit H57, while the output of the channel amplifier A2 is directly connected to one output of each of the subtracting circuits H58, H59 and H60. The output of the channel amplifier A1 is connected through the multiplier circuit M60 to the other input of the subtracting circuit H58, and the output of the channel amplifier A3 is connected through the multiplier circuits M69, M70 and M71 to the other input of each of the subtracting circuits H59, H60 and H57. Depending on the sequence, the output signals of the subtracting circuits H57, H58, H59 and H60 can be expressed by the functions $f(C_1, C_2)$, $f(C_2, C_3)$, $f(C_1, C_2)$, $f(C_2, C_3)$.

Figure 23:
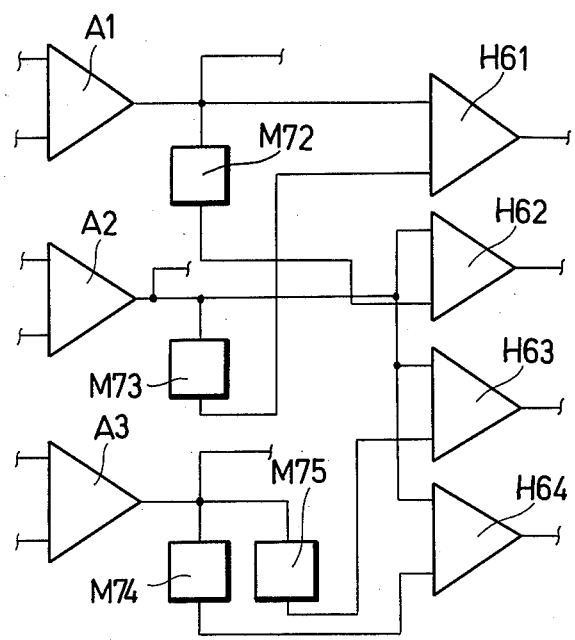

In another embodiment according to FIG. 23, the output of the channel amplifier A1 is connected directly to one input of the subtracting circuit H61, but the output of the channel amplifier A2 is directly connected to one input of each of the subtracting circuits H62, H63 and H64, while on the other hand the output of the channel amplifier A1 is connected through the multiplier circuit M72 to the other input of the subtracting circuit H62 and the output of the channel amplifier A2 is connected through the multiplier circuit M72 to the other input of the subtracting circuit H61 and the output of the channel amplifier A3 is connected through the multiplier circuits M74 and M75 to the other input of each of the subtracting circuits H64 or H63. Depending on the sequence, the output signals of the subtracting circuits can thus be expressed by the functions $f(C_1, C_2)$, $f(C_2, C_3)$, $f(C_1, C_2)$ and $f(C_2, C_3)$.

Figure 24:
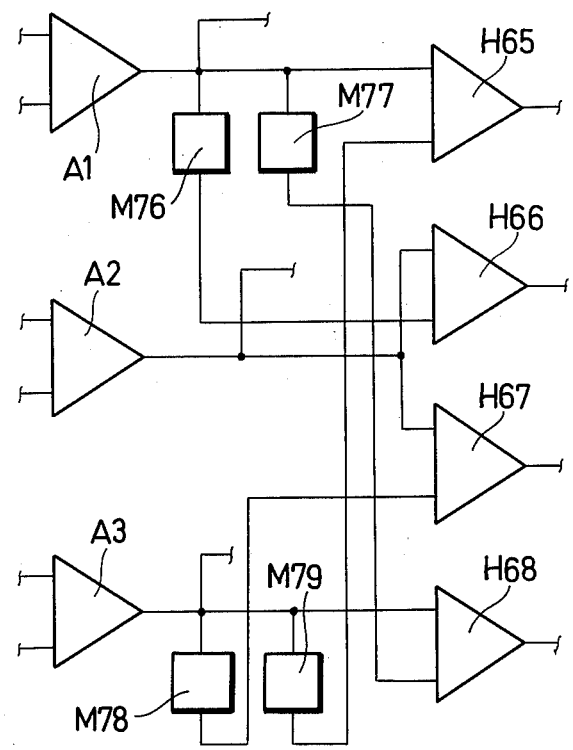

The embodiment according to FIG. 24 is as follows. The output of the channel amplifier A1 is connected directly to one input of the subtracting circuit H65, the output of the channel amplifier A2 is directly connected to one input of each of the subtracting circuits H66 and H67 and the output of the channel amplifier A3 is directly connected to one input of the subtracting circuit H68. At the same time, the output of the channel amplifier A1 is connected through the multiplier circuits M76 and M77 to the other input of each of the subtracting circuits H66 and H68, the output of the channel amplifier A3 is connected through the multiplier circuits M78 and M79 to the other input of each of the subtracting circuits H67 and H65. Depending on the sequence, the output signals of the subtracting circuits can thus be expressed by the functions $f(C_1, C_2)$, $f(C_1, C_2)$, $f(C_2, C_3)$ and $f(C_2, C_3)$.

Figure 25:
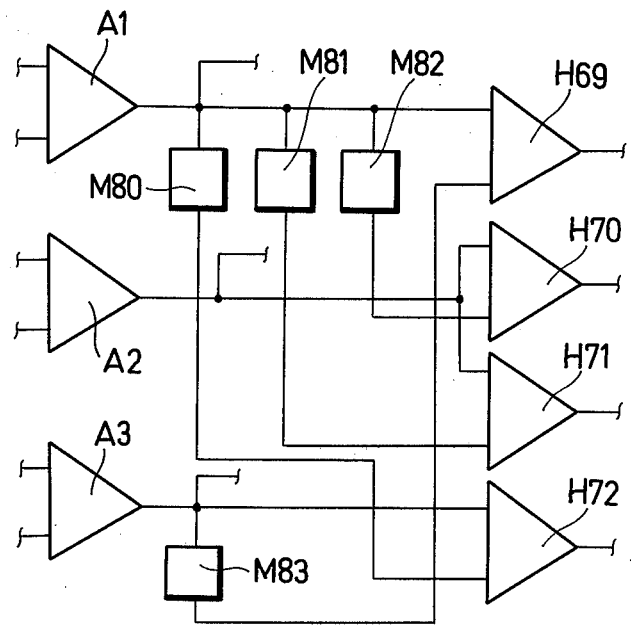

In the embodiment according to FIG. 25, the output of the channel amplifier A1 is connected directly to one input of the subtracting circuit H69, the output of the channel amplifier A2 is directly connected to one input of the subtracting circuit H70 and H71, and the output of the channel amplifier A3 is directly connected to one input of the subtracting circuit H72. At the same time, the output of the channel amplifier A1 is connected through the multiplier circuits M80, M81 and M82 to the other input of each of the subtracting citcuits H72, H71 and H70 and the output of the channel amplifier A3 is connected through the multiplier circuit M83 to the other input of the subtracting circuit H69. Depending on the sequence, the output signals of the subtracting circuits H69, H70, H71 and H72 can thus be expressed by the functions $f(C_1, C_2)$, $f(C_1, C_2)$, $f(C_2, C_3)$ and $f(C_2, C_3)$.

Figure 26:
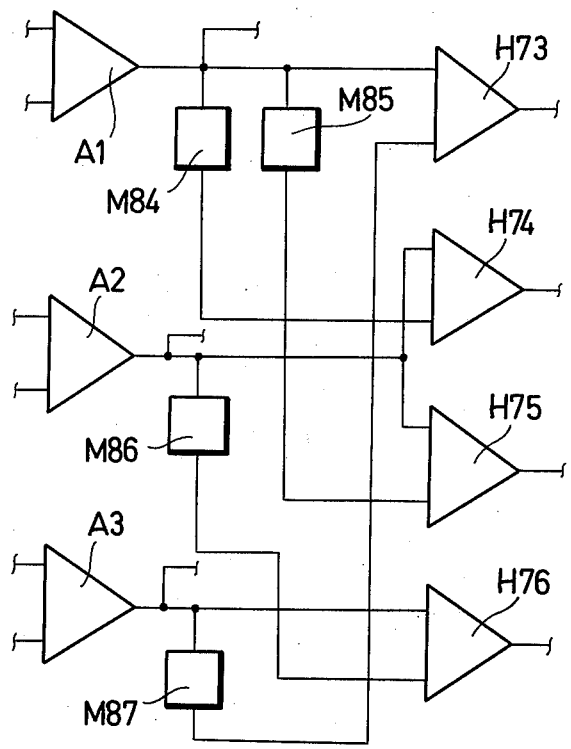

In another embodiment according to FIG. 26, the output of the channel amplifier A1 is connected directly to one input of the subtracting circuit H73, the output of the channel amplifier A2 is directly connected to one input of each of the subtracting circuits H74 and H75, the output of the channel amplifier A3 however is directly connected to one input of the subtracting circuit H76.

At the same time, the output of the channel amplifier A1 is connected through the multiplier circuits M84 and M85 to the other input of each of the subtracting circuits H74 and H75, the output of the channel amplifier A2 is connected through the multiplier circuit M86 to the other input the subtracting circuit H76, the output of the channel amplifier A3 is connected through the multiplier circuit M87 to the other input of the subtracting circuit H73. Depending on the sequence, the output signals of the subtracting circuits H73 – H76 are therefore expressed by the functions $f(C_1, C_2)$, $f(C_1, C_2)$, $f(C_2, C_3)$ and $f(C_2, C_3)$.

Figure 27:
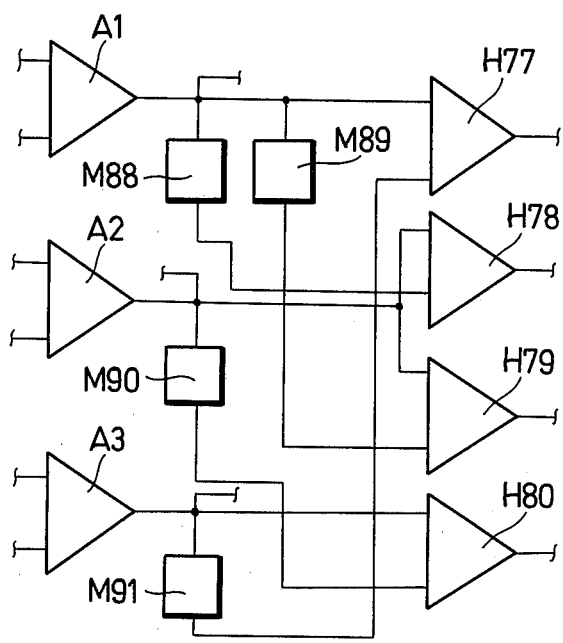

In the embodiment according to FIG. 27, the output of the channel amplifier A1 is connected directly to one input of the subtracting circuit H77, the output of the channel amplifier A2 is directly connected to one input of each of the subtracting circuits H78 and H79, the output of the channel amplifier A3 is directly connected to one input of the subtracting circuit H80. At the same time, the output of the channel amplifier A1 is connected through the multiplier circuits M88 and M79 to each of the other inputs of the subtracting circuits H78 and H79, the output of the channel amplifier A2 is connected through the multiplier circuit M90 to the other input of the subtracting circuit H80 and the output of the channel amplifier A3 is connected through the multiplier circuit M91 to the other input of the subtracting circuit H77. Depending on the sequence, the output signals of the subtracting circuits H77, H78, H79 and H80 can be expressed by the functions $f(C_1, C_2)$, $f(C_2, C_3)$, $f(C_1, C_2)$ and $f(C_2, C_3)$.

Figure 28:
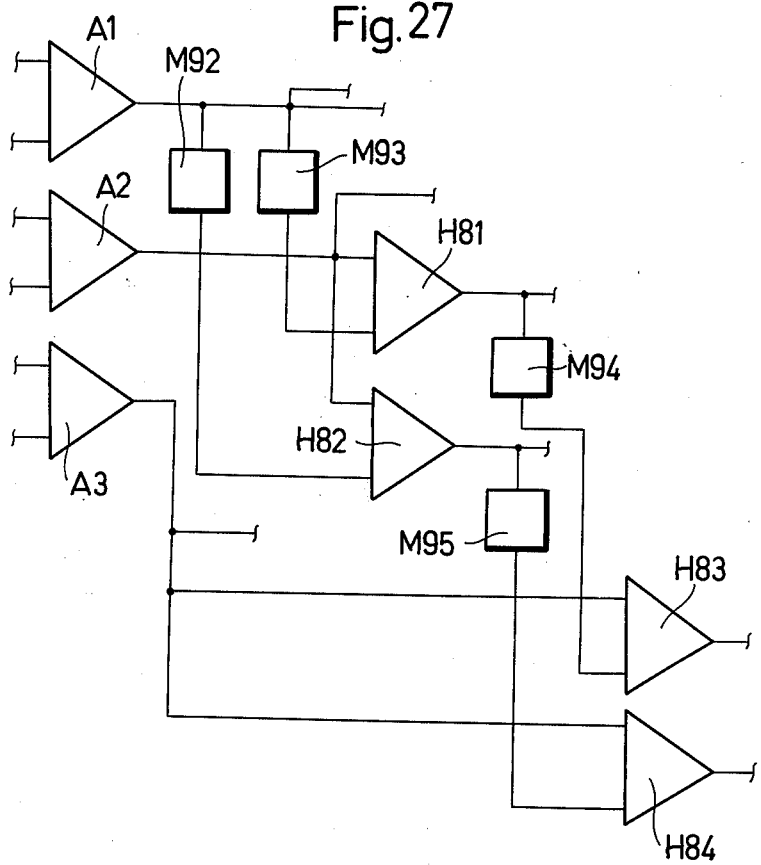

In the embodiment according to FIG. 28, the output of the channel amplifier A2 is connected directly to one input of the subtracting circuits H81 and H82 and the output of the channel amplifier A3 is directly connected to one input of each of the subtracting circuits H83 and H84. At the same time, the output of the channel amplifier A1 is connected through the multiplier circuits M82 and M93 to the other input of each of the subtracting circuits H82 and H81 and the output of the subtracting circuit H81 is connected through the multiplier circuit M94 and the output of the subtracting circuit H82 is connected through the multiplier circuit M95 to the other input of the subtracting circuits H83 and H84. Depending on their sequence, the output signals of the subtracting circuits H81, H82, H83 and H84 can be expressed by the functions $f(C_1, C_3)$, $f(C_2, C_3)$, $f(C_2, C_3)$ and $f(C_1, C_3)$.

Figure 29:
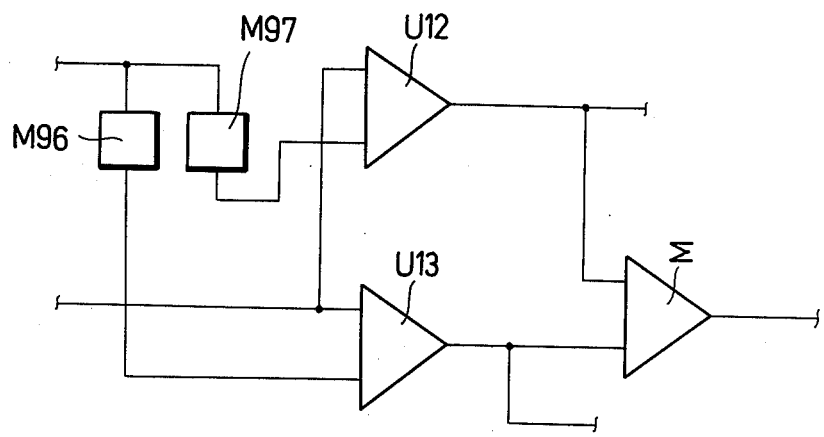
Figure 30:
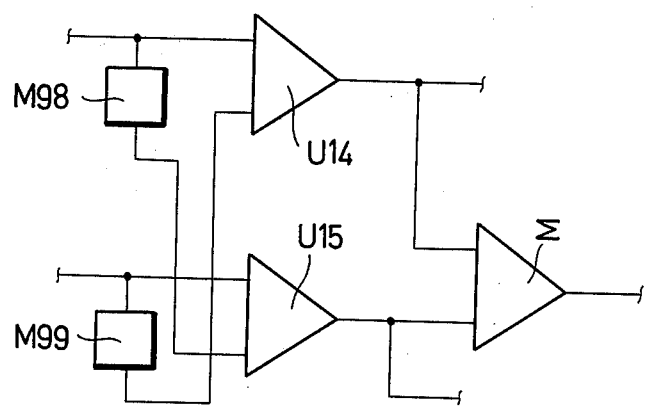
Figure 31:
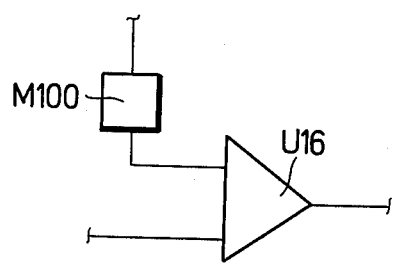

Further processing of the signals on the outputs of the subtracting circuits according to FIGS. 16-28 containing two unknown concentration values and each of them representing a linear equation is performed by means of the circuits illustrated in FIGS. 29, 30 and 31.

Figure 15:
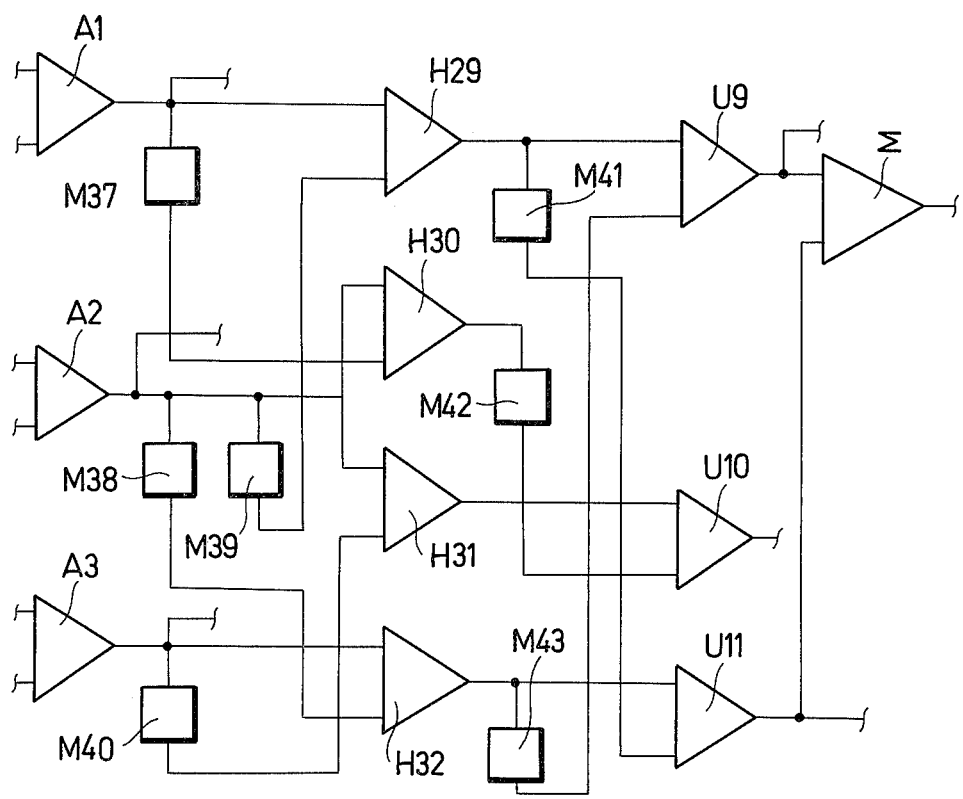
FIGs. 15–28 show further embodiments of the invention according to FIGS. 3 and 4, and FIGS. 29–31 show further embodiments of the invention according to FIGS. 15–28.

If the output of the subtracting circuit H29 (FIG. 15) is connected via the multiplier circuits M96 and M97 to one input of each of the subtracting or scale setting circuits U13 and U12 and the output of the subtracting circuit H32 is connected directly to the other input of the subtracting and scale setting circuits U12 and U13, a signal proportional to the concentration $C_1$ will be produced at the output of the subtracting and scale setting circuits U12 and a signal proportional to the concentration $C_2$ will be produced at the output of the subtracting and scale setting circuit U13 (see FIGS. 15 and 29).

In like manner if one output of each of the subtracting circuits H33 (FIG. 16) or H37 (FIG. 17) or H41 (FIG. 18) or H45 (FIG. 19) or H49 (FIG. 20) or H53 (FIG. 21) or H57 (FIG. 22) or H61 (FIG. 23) or H65 (FIG. 24) or H69 (FIG. 25) or H73 (FIG. 26) or H77 (FIG. 27) is connected through the multiplier circuit M96 and M97 (FIG. 29) to one input of each of the subtracting and scale setting circuits U13 and U12 and furthermore if one output of each of the subtracting circuits H36 (FIG. 16) or H39 (FIG. 17) or H42 (FIG. 18) or H47 (FIG. 19) or H51 (FIG. 20) or H54 (FIG. 21) or H59 (FIG. 22) or H63 (FIG. 23) or H66 (FIG. 24) or H70 (FIG. 25) or H74 (FIG. 26) or H79 (FIG. 27) is directly connected to the other input of each of the subtracting and scale setting circuits U12 and U13 a signal, proportional to the concentration $C_1$ and the signal, proportional to the concentration $C_2$ will be produced at the output of the subtracting and scale setting circuits U12 and U13.

In accordance with the previous statements, the signals which are proportional to the concentration $C_1$ and $C_2$ can be determined in such a way that the output of the subtracting circuit H33 (FIG. 16) or H37 (FIG. 17) or H41 (FIG. 18) or H46 (FIG. 19) or H49 (FIG. 20) or H53 (FIG. 21) or H57 (FIG. 22) or H61 (FIG. 23) or H65 (FIG. 24) or H69 (FIG. 25) or H73 (FIG. 26) or H77 (FIG. 27) on the one hand are directly connected to one input of the subtracting and scale setting circuit U14 and on the other hand are connected through the multiplier circuit M98 to one input of the subtracting and scale setting circuit U15 and furthermore, if the output of the subtracting circuit H36 (FIG. 16) or H39 (FIG. 17) or H42 (FIG. 18) or H47 (FIG. 19) or H51 (FIG. 20) or H54 (FIG. 21) or H59 (FIG. 22) or H63 (FIG. 23) or H66 (FIG. 24) or H70 (FIG. 25) or H74 (FIG. 26) or H79 (FIG. 27) on the one hand is directly connected to the other input of the subtracting and scale setting circuit U15 and on the other hand is connected through the multiplier circuit M99 to the other input of the subtracting and scale setting circuit U14. The signal which is proportional to the concentration $C_1$ and the signal, proportional to the concentration $C_2$ will appear at the output of the subtracting and scale setting circuits U14 and U15 (see FIG. 30).

The third concentration value $C_3$ is determined by the circuit in accordance with FIG. 31:

The output of the subtracting circuit H34 (FIG. 16) or H38 (FIG. 17) or H43 (FIG. 18) or H46 (FIG. 19) or H50 (FIG. 20) or H55 (FIG. 21) or H58 (FIG. 22) or H62 (FIG. 23) or H67 (FIG. 24) or H71 (FIG. 25) or H75 (FIG. 26) or H78 (FIG. 27) is connected via the multiplier circuit M100 to one input of the subtracting and scale setting circuit U16, the output of the subtracting circuit H35 (FIG. 16) or H40 (FIG. 17) or H44 (FIG. 18) or H48 (FIG. 19) or H52 (FIG. 20) or H56 (FIG. 21) or H60 (FIG. 22) or H64 (FIG. 23) or H68 (FIG. 24) or H72 (FIG. 25) or H76 (FIG. 26) or H80 (FIG. 27) is directly connected to the other input of the subtracting and scale setting circuit U16. A signal which is proportional to the concentration $C_3$ will be produced in this case at the output of the subtracting and scale setting circuit U16.

Signals produced at the output of the circuits 29, 30 and 31 illustrated in FIG. 28 are processed by analogy.

What we claim is:

1. An apparatus for determining the concentration of a dye in a biological liquid, such as blood, comprising an optical sensing system, a counting system, a feed and control system and an indicating apparatus, said counting system having an input with three channels in accordance with the number of channels of the optical system, each of said channels of said counting system having a logarithmic circuit or the three channels together having a logarithmic circuit operating in time multiplex operation, and having three amplifiers, and four subtraction circuits connected to said channel amplifiers; three subtraction and scale setting circuits, each having an input, the outputs of said subtraction circuits being connected to the inputs of said three subtraction and scale setting circuits; a summing circuit; quotient forming circuit means; any two of the outputs of the last mentioned subtraction and scale setting circuits being connected to the input of said summing circuit, and the output of said summing circuit being connected to said indicating apparatus and to the input of said quotient forming circuit means; the outputs of said subtraction and scale setting circuits being connected to the quotient forming circuit means; the outputs of the quotient forming circuit means being connected to said indicating apparatus; and a fine adjustment potentiometer connected to further inputs of said quotient forming circuit means.

2. An apparatus according to claim 1, wherein said subtraction circuits are connected to said channel amplifiers via one multiplication circuit each, and to the inputs of said three subtraction and scale setting circuits via one multiplication circuit each.

3. An apparatus according to claim 1, wherein said quotient forming circuit means is a quotient forming circuit.

4. An apparatus according to claim 1, wherein said quotient forming circuit means is a quotient forming and multiplying circuit, and wherein at least one fine adjustment potentiometer is connected to the further inputs of said quotient forming and multiplying circuit.

5. An apparatus for determining the concentration of a dye in a biological liquid, such as blood, comprising an optical sensing system, a counting system, a feed and control system and an indicating apparatus, said counting system having an input with three channels in accordance with the number of channels of the optical system, each of said channels of said counting system having a logarithmic circuit or the three channels together having a logarithmic circuit operating in time multiplex operation, and having three amplifiers, and three subtraction circuits connected to said channel amplifiers, a plurality of subtraction and scale setting circuits; the outputs of said three subtraction circuits following the channel amplifiers being connected to said subtraction and scale setting circuits and to the input of a single subtraction circuit, the output of the last-mentioned single subtraction circuit being connected to the input of one of said subtraction and scale setting circuits; a summing circuit; quotient forming circuit means; the output of said last-mentioned subtraction circuit being furthermore connected to the input of one of said scale setting circuits and the output of said last-mentioned scale setting circuit as well as one of the outputs of said subtraction and scale setting circuits or the outputs of said two last-mentioned subtraction and scale setting circuits being connected to the input of said summing circuit; the output of said summing circuit being connected to the input of said quotient forming circuit means and to the input of said indicating device; the outputs of said scale setting circuit as well as the outputs of said subtraction and scale setting circuits being connected to the indicating device and to the input of the quotient forming circuit means; the outputs of the quotient forming circuit means being connected to said indicating device; and a fine adjustment potentiometer connected to further inputs of said quotient forming circuit means.

6. An apparatus according to claim 5, wherein said subtraction circuits are connected to said channel amplifiers via one multiplication circuit each, and to the inputs of said three subtraction and scale setting circuits via one multiplication circuit each.

7. An apparatus according to claim 5, wherein said quotient forming circuit means is a quotient forming circuit.

8. An apparatus according to claim 5, wherein said quotient forming circuit means is a quotient forming and multiplying circuit, and wherein at least one fine adjustment potentiometer is connected to the further inputs of said quotient forming and multiplying circuit.

* * * * *